United States Patent [19]

Payne et al.

[11] Patent Number: 5,741,960
[45] Date of Patent: Apr. 21, 1998

[54] PROBE CHROMATOGRAPH APPARATUS AND METHOD

[75] Inventors: Glen D. Payne; Wallace J. Trochesset; Edward M. Browne, all of Houston, Tex.

[73] Assignee: Daniel Industries, Inc., Houston, Tex.

[21] Appl. No.: 250,440

[22] Filed: May 27, 1994

[51] Int. Cl.⁶ ................................................. B01D 15/08
[52] U.S. Cl. ................................................. 73/23.41; 422/89
[58] Field of Search ....................... 73/23.35, 23.41; 422/89

[56] References Cited

U.S. PATENT DOCUMENTS

| | | | |
|---|---|---|---|
| 3,772,909 | 11/1973 | Anderson | 73/23.41 |
| 3,798,973 | 3/1974 | Estey | 73/23.35 |
| 3,926,561 | 12/1975 | Lucero | 73/23.35 |
| 4,159,894 | 7/1979 | Hu | 73/23.41 |
| 4,704,141 | 11/1987 | Krebber | 73/23.41 |
| 4,872,334 | 10/1989 | Watanabe | 73/23.35 |
| 4,999,162 | 3/1991 | Wells et al. | 422/89 |
| 5,006,315 | 4/1991 | Maroulis et al. | 73/23.35 |
| 5,014,541 | 5/1991 | Sides et al. | 73/23.41 |
| 5,109,710 | 5/1992 | Newkirk et al. | 73/23.41 |
| 5,114,439 | 5/1992 | Yost et al. | 55/20 |
| 5,235,843 | 8/1993 | Langhorst | 73/19.02 |
| 5,240,604 | 8/1993 | Cortes et al. | 210/198.2 |
| 5,340,543 | 8/1994 | Annino et al. | 73/23.35 |
| 5,376,277 | 12/1994 | Cortes et al. | 210/659 |

FOREIGN PATENT DOCUMENTS

| | | | |
|---|---|---|---|
| 2210023 | 6/1989 | United Kingdom | 73/23.41 |
| 2243411 | 10/1991 | United Kingdom | 73/23.41 |

*Primary Examiner*—Richard Chilcot
*Assistant Examiner*—Eric S. McCall
*Attorney, Agent, or Firm*—Alton W. Payne

[57] ABSTRACT

A probe chromatograph apparatus and method is provided which engages directly the process stream from which the sample is taken. The probe chromatograph apparatus is a simple, miniaturized chromatograph installed directly into the source pipeline or vessel. An analyzer mechanism extends through a pipe nipple into the fluid flow from which the sample is drawn. A sampling mechanism transfers a fixed volume of sample into the probe chromatograph apparatus. Means for separating the sample into its constituents is provided, and a detector is provided for sensing and measuring the quantity of the respective constituents.

36 Claims, 19 Drawing Sheets

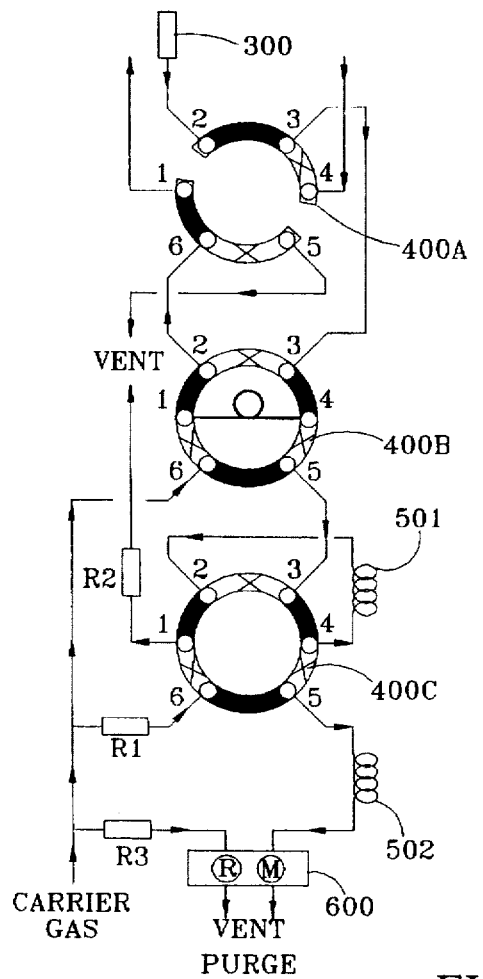
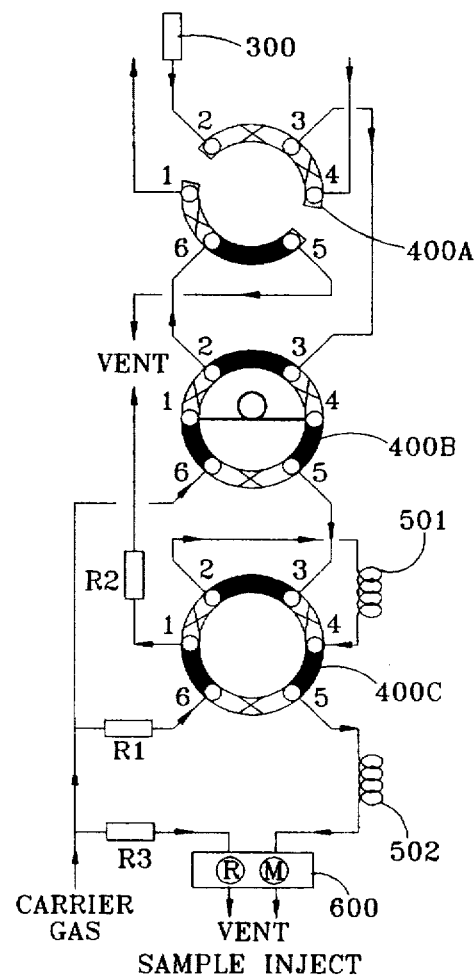
FIG.5 PURGE / SAMPLE INJECT
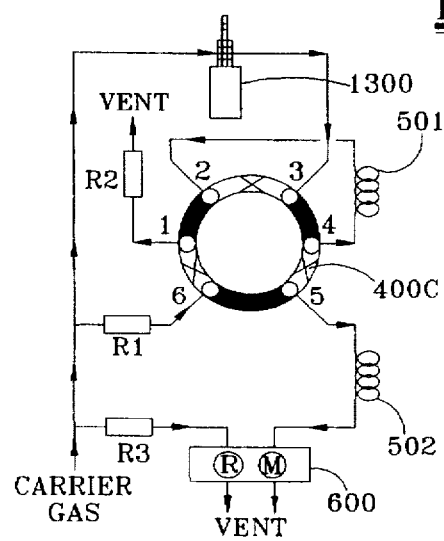
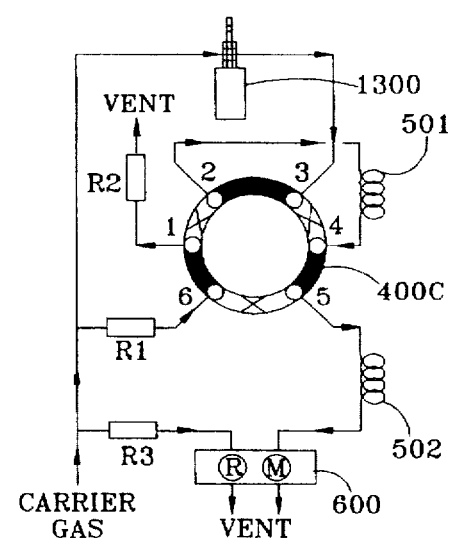
FIG.6 PURGE / SAMPLE INJECT

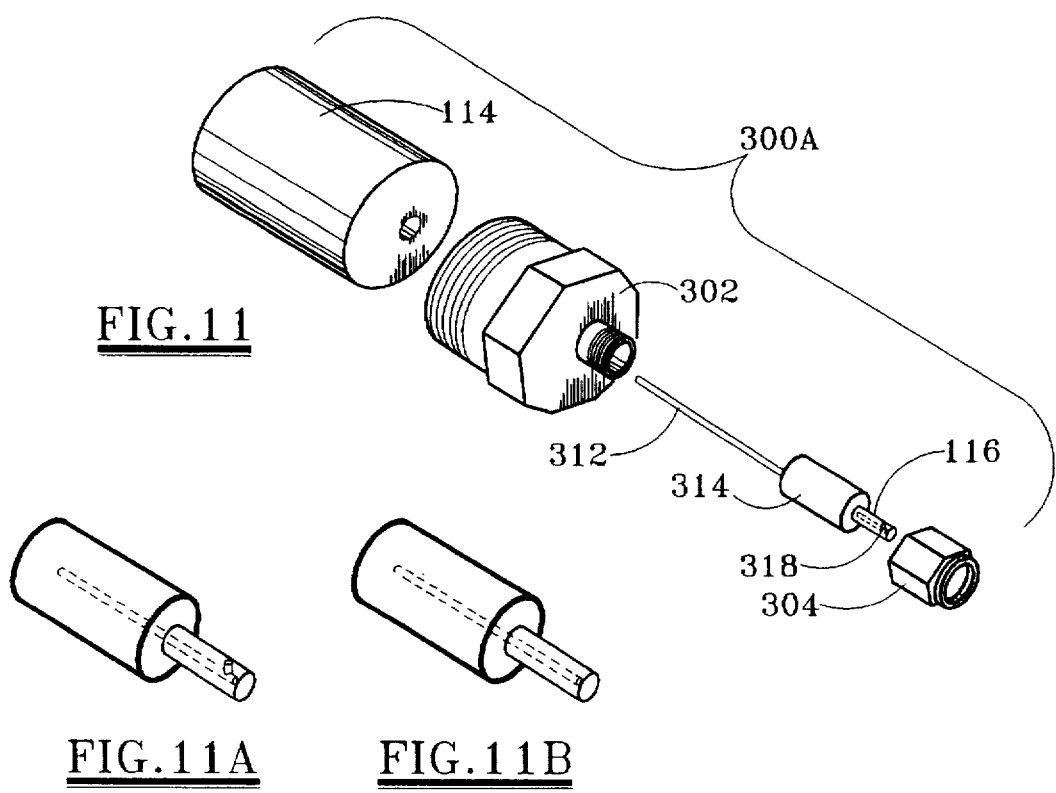
FIG.11
FIG.11A   FIG.11B
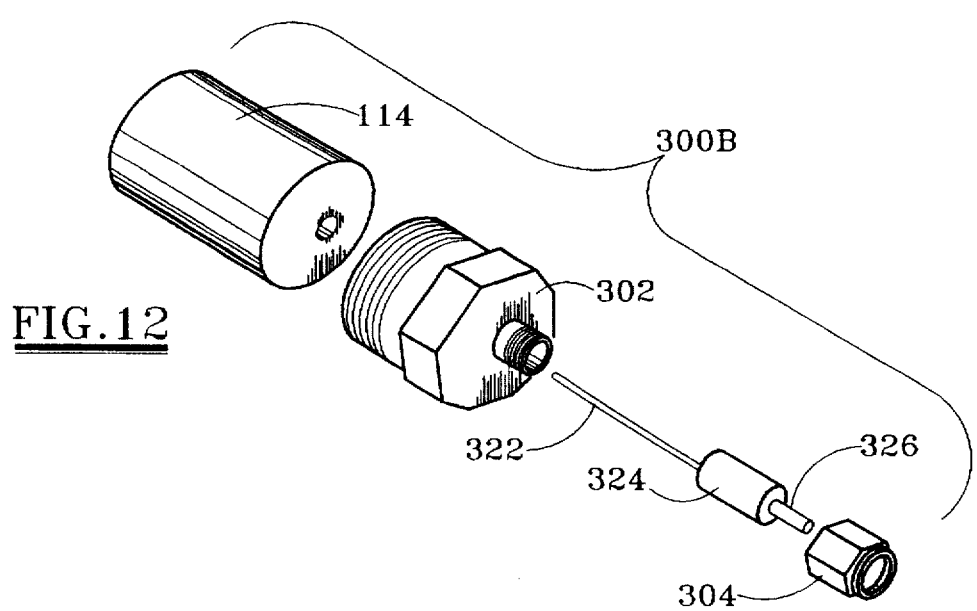
FIG.12

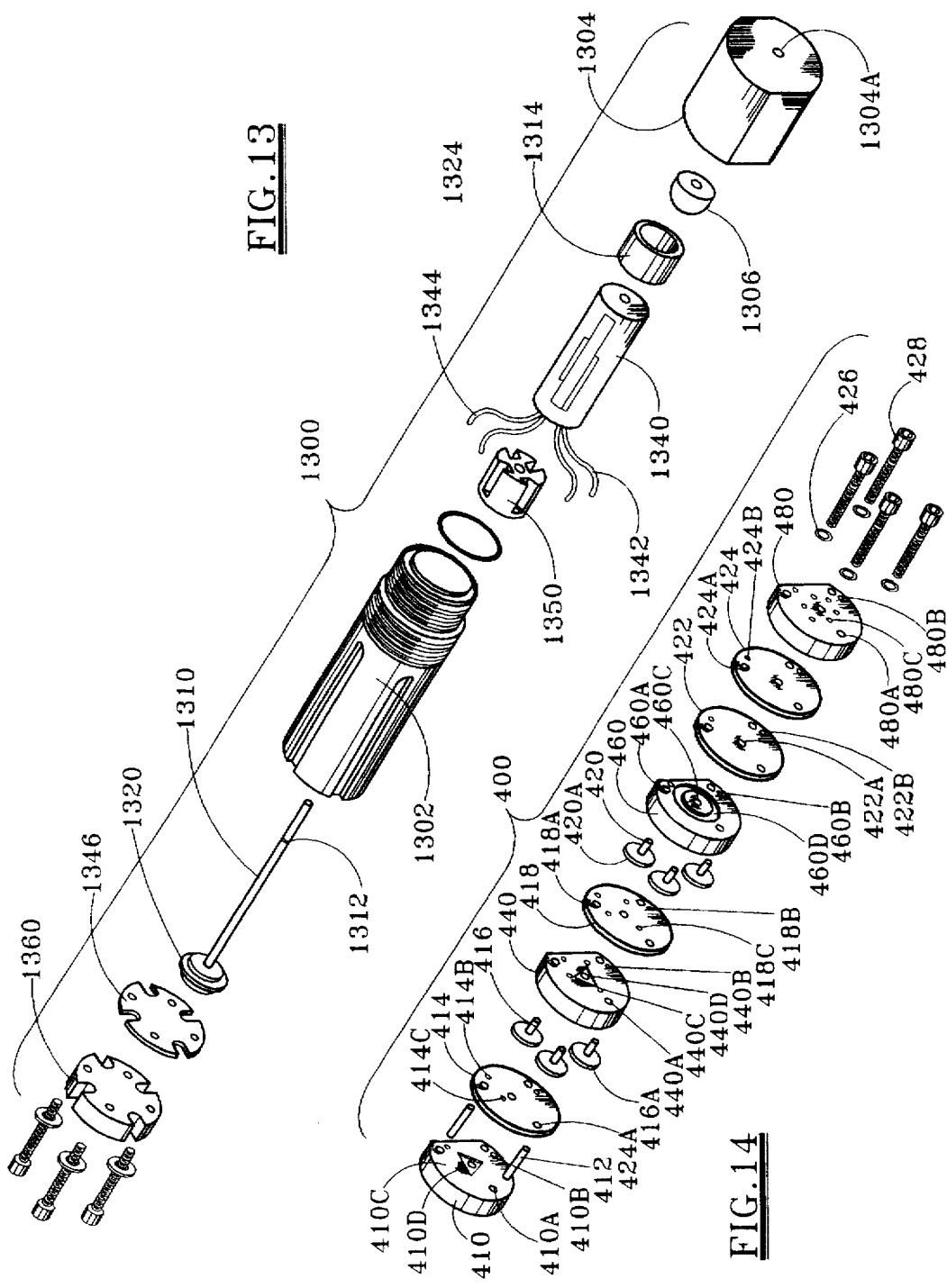

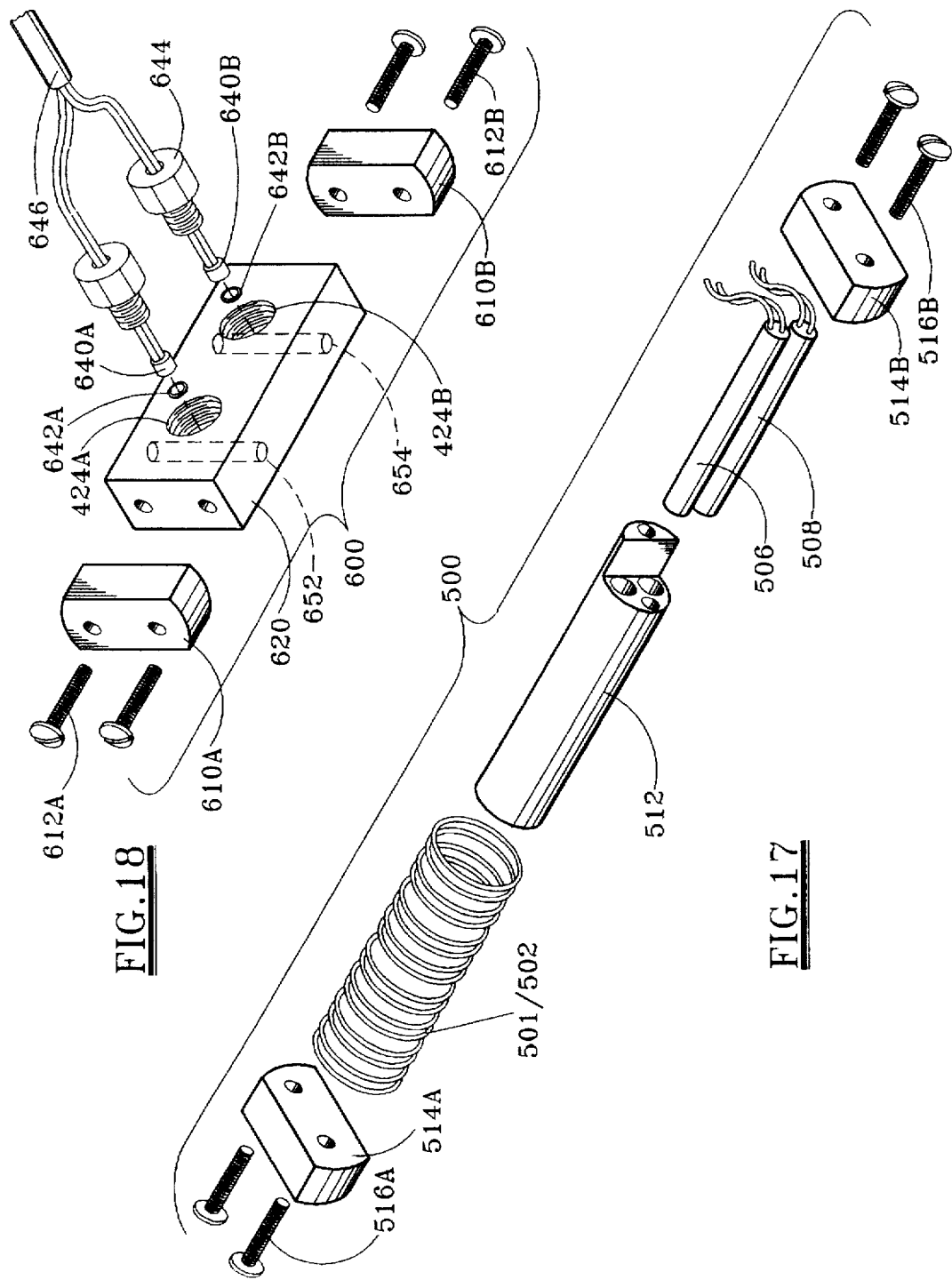

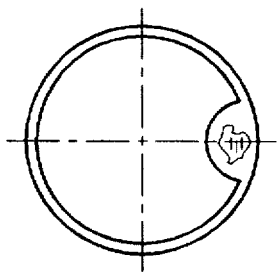
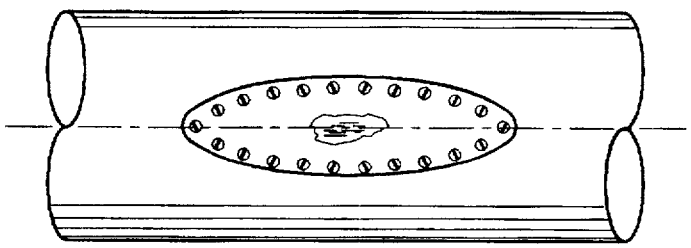
FIG.19A        FIG.19B
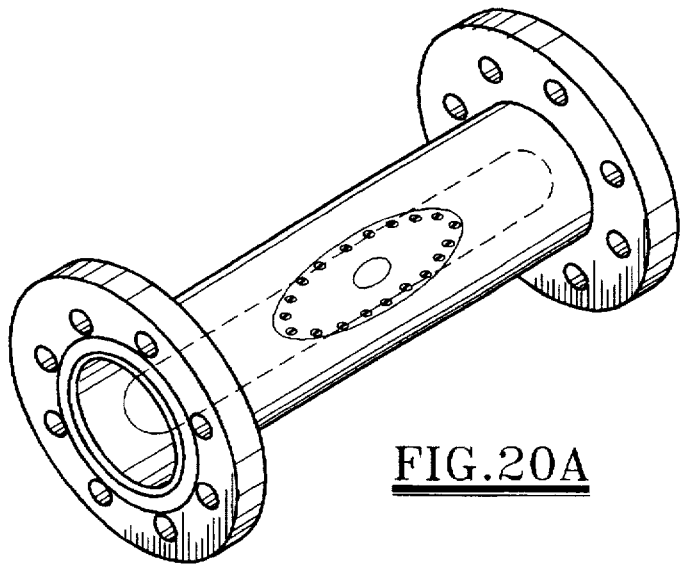
FIG.20A
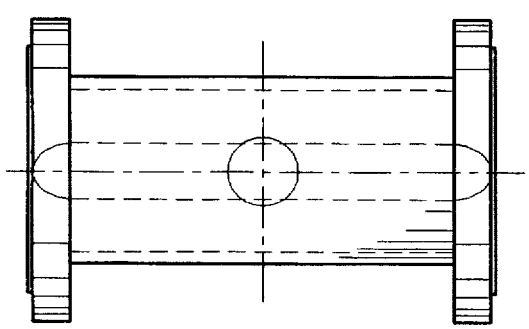
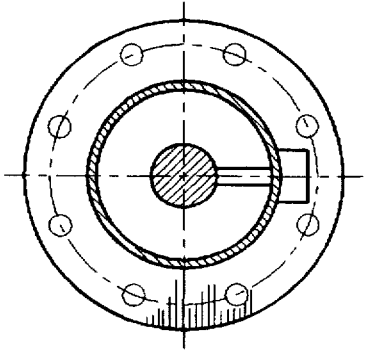
FIG.20B        FIG.20C

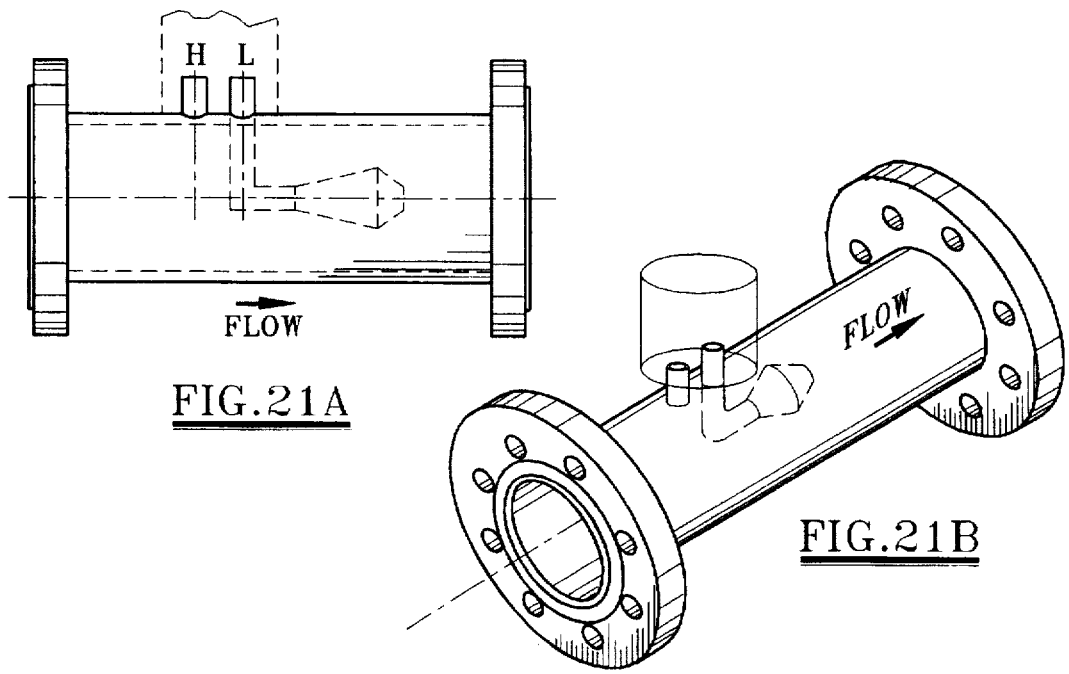
FIG.21A
FIG.21B
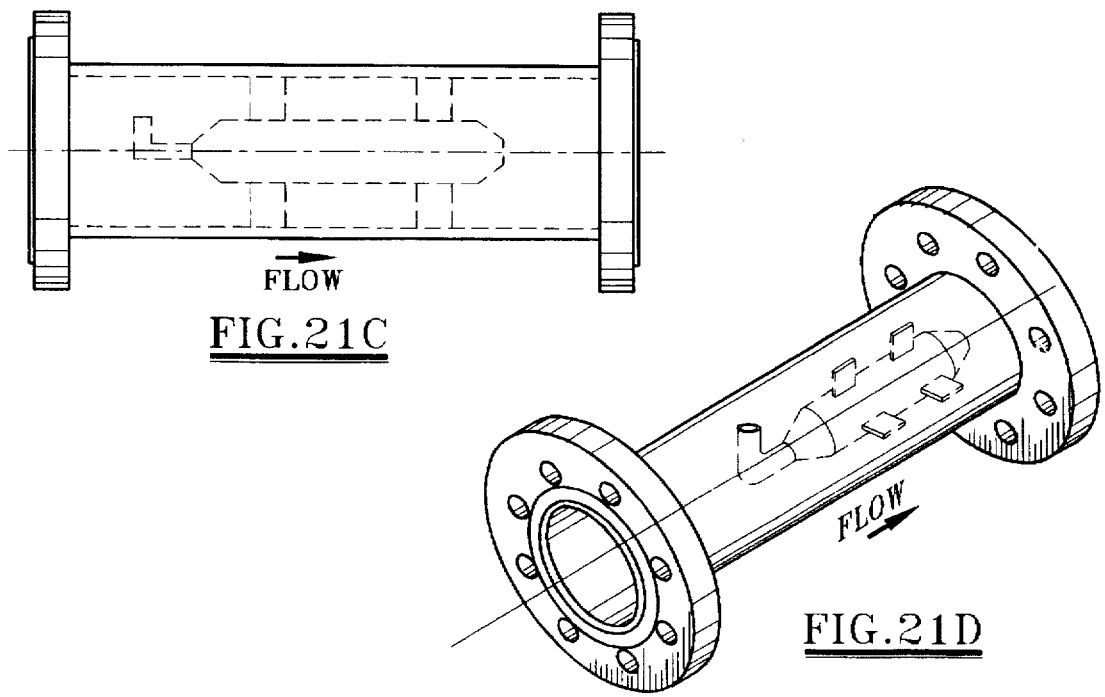
FIG.21C
FIG.21D

PROBE CHROMATOGRAPH APPARATUS AND METHOD

FIELD OF THE INVENTION

The present invention relates generally to chromatography. More particularly, the present invention relates to a stand-alone, miniaturized, chromatograph installed directly in the process fluid without a sample conditioning system.

BACKGROUND OF THE INVENTION

Historically, a chromatograph system consisted of a sample conditioning system, a sample injector, a separating column, a detector, and a carrier gas flowing through the components in series. A sample of fluid (gas or liquid) to be analyzed was introduced into the flowing carrier gas through the sample injector, and carried through the separating column and detector. The components of the sample have varying degrees of attraction for the material in the column. Thus, the time to elute from the column to the detector is proportional to the strength of the attraction between the components of the sample and the material in the column. The effluent from the column is coupled to a detector and related electronics. With time and sufficient data, the chromatograph became an important qualitative tool for identifying components and compounds based on their elution order and/or time of elution.

For the chromatograph to become quantitative required more precise detectors, precision temperature and flow control, uniformity in manufacturing columns, and precision sample injectors. The quantity measurement of any component is based on the component mixed with the carrier gas during the elution time. Most detectors measure the quantity of any component as a change in thermal conductivity or electron transfer. Generally, the thermal conductivity is measured relative to the undiluted carrier gas of known thermal conductivity.

For a chromatograph to become a useful process analyzer, it must adapt to the process environment. This requires elaborate sample preparation and automated sample injection. Further, a chromatograph must meet stringent electrical classifications, have appropriate climate protection, and exhibit reliable, low maintenance operation. Because of the size and expense of such a system, the analyzer is often designed to analyze multiple samples and is normally located in a sheltered area remote from the sample point. The sample injector, separating columns, and detector are usually installed inside a large temperature controlled oven with circulating air as the heating medium. Samples from the process stream must be transported to the analyzer without destroying their integrity. Often sample transfer necessitates heating the entire sample line for extended distances. Safety and environmental constraints generally require that the unused sample be returned back to the process.

In the present invention the sample primary conditioning system, the sample transport, the sample conditioning system, and the sample return disposal are eliminated. The processing of the sample begins within the vessel or conduit, but may finish within or outside depending upon the design.

A feature of the present chromatographic system and method is to change the concept of construction and the size of the chromatograph to enable the installation of the chromatograph directly into the process vessel and into the flow of the fluid to be measured.

Another unique feature of the present chromatographic system and method is that the invention eliminates the need for the sample conditioning system, the sample transfer lines (and their temperature control), as well as a large air-bath temperature controlled oven.

A feature of the present chromatographic system and method of the present invention relates to the concept of construction and installation which eliminates the need for a climate-controlled shelter. By using the chromatographic system and method of the present invention directly in the process pipe or vessel in direct contact with the process fluid, the applicable process applications are only limited by the temperature range of the analyzer.

Another feature of the present chromatographic system is to provide chromatographic components which are installed inside a stainless steel probe and the control electronics are installed inside an explosion-proof conduit attached to the probe.

Yet another feature of the present chromatographic system of the present invention is that it can be installed in an area classified as hazardous.

Due to the method of installation associated with the present invention, a feature of the probe chromatographic analyzer is that, if it fails, the analyzer can be removed from the process vessel and exchanged with another analyzer to allow fast, easy maintenance without the delay time associated with attempting to repair a conventional on-line unit.

Another feature of the present invention is to reduce the lag time between sampling and analysis due to the sampling within the source of the fluid. Ordinarily, samples that travel through long sample lines and sample conditioning systems are significantly delayed, which reduces the ability to effectively control a process. Such lag time is not present in the present invention.

Still another feature of the present invention is to provide a probe chromatograph apparatus which itself becomes the sample probe. The chromatograph apparatus of the present invention is introduced into the process fluid flow directly or with a small internal filter to condition the sample. Such a filter can be the sample tip itself, for instance when made from sintered metal, or installed in the sample line immediately after the probe tip. Since the volume of the sample is small compared to the conventional sample system, elaborate sample conditioning is not required.

Additional features of the invention will be set forth in part in the description which follows, and in part will become apparent from the description, or may be learned by practice of the invention. The features and advantages of the invention may be realized by means of the combinations and steps particularly pointed out in the appended claims.

SUMMARY OF THE INVENTION

To achieve the foregoing features, and advantages and in accordance with the purpose of the invention as embodied and broadly claimed herein, a probe chromatographic apparatus and method are provided for extracting a sample directly from a fluid into the chromatograph without the need of conventional sampling systems or temperature control.

In one embodiment, a method of making chromatographic measurements at the location of sampling of a fluid, rather than at a remote location, is provided. The fluid is in a conduit, vessel or reactor. The method comprises the steps of acquiring a sample within the conduit/vessel, beginning processing of the acquired sample within the conduit/vessel, and detecting characteristics of the fluid.

Also encompassed by the present invention, after the step of beginning processing, the step of completing processing of the acquired sample within the conduit/vessel is provided. Further, the step of completing processing of the acquired sample can be outside the conduit/vessel. The step of detecting characteristics of the fluid includes detecting within the conduit/vessel and detecting outside the conduit/vessel.

The step of acquiring a sample within the conduit/vessel includes accepting the sample via a tip engaged in the fluid, the tip having an aperture and a channel for transferring the fluid. The tip can be shaped or shielded, and include an aperture on the side or on the end. The aperture can have a geometric shape, e.g., circle, square, etc.

Another embodiment includes accepting the sample via a plunger removeably engaged in the fluid. The plunger can be shaped or shielded, and grooved, slotted or with a hole.

Another embodiment includes accepting the sample via a porous member. The porous member can be sintered, membraned or woven.

The method includes separating the sample into components essentially at the point of acquisition and using a chromatographic column. The fluid is separated based upon its physical or chemical properties. Preferrably, the step of detecting the characteristics of the fluid comprises detecting the characteristics using the thermal conductivity of the fluid.

In another embodiment, a probe chromatograph apparatus for making chromatographic measurements at the location of sampling of a fluid, rather than at a remote location, is provided. The probe chromatograph apparatus comprises a sampler for acquiring a sample within the conduit/vessel, a processor for initiating processing of the acquired sample within the conduit/vessel, and a detector for detecting characteristics of the fluid. A flame path arrester is between the probe and the vessel. The sampler promptly provides the processor a sample of predetermined volume. The probe chromatograph includes an explosion proof containment.

In more detail, the probe chromatograph includes a housing for securing the sampler, the processor and the detector, a connector for removeably engaging the housing with the conduit/vessel such that the sampler and at least part of the processor is inside the conduit/vessel, a flame-path plug for securing the probe and the conduit/vessel from flame communication there between, a valve for segregating the sample forthwith into sample portions, a chromatographic separator for receiving the sample portions for separation, and a detector in operative association with the chromatographic separator for accepting the sample portions segregated by the chromatographic separator and for detecting the characteristics of the fluid.

The probe chromatograph can include an enclosure for containing the probe within the conduit/vessel. Also, the probe chromatograph can further include a flow measuring device for determining the total energy flux within the conduit/vessel.

BRIEF DESCRIPTION OF THE DRAWINGS

The accompanying drawings which are incorporated in and constitute a part of the specification, illustrate a preferred embodiment of the invention and together with the general description of the invention given above and the detailed description of the preferred embodiment given below, serve to explain the principles of the invention.

FIG. 5 is a schematic flow diagram showing examples of sample fluid and carrier gas paths associated with the preferred valves inside the probe chromatographic apparatus of the present invention.

FIG. 6 is a schematic flow diagram showing different sampling technique along with the carrier gas paths associated with the preferred valves inside the probe chromatographic apparatus of the present invention.

FIG. 11 is a partial, exploded view of one embodiment of a sampler assembly using a capillary sample tip as taught by the present invention.

FIG. 12 is a partial, exploded view of another embodiment of a sampler assembly using a porous metal sample tip as taught by the present invention.

FIG. 13 is a partial, exploded view of the liquid sampler assembly as taught by the present invention.

FIG. 14 is an exploded view of a multi-port mini-valve as taught by the present invention.

FIG. 17 illustrates an exploded view of one embodiment of a separating column assembly as taught by the present invention.

FIG. 18 is a partially-exploded view of one embodiment of a detector as taught by the present invention.

FIGS. 19A and 19B illustrate an optional embodiment of the present invention showing the probe integrated on the side of the process vessel or conduit.

FIGS. 20A, 20B and 20C illustrate an optional embodiment of the probe present invention showing the probe inside the fluid conduit with effluent flowing on all sides.

FIGS. 21A, 21B, 21C and 21D illustrate another embodiment of the present invention incorporating a fluid flow measurement for determining a total energy measurement.

The above general description and the following detailed description are merely illustrative of the generic invention, and additional modes, advantages, and particulars of this invention will be readily suggested to those skilled in the art without departing from the spirit and scope of the invention.

DETAILED DESCRIPTION OF THE PREFERRED EMBODIMENTS

Reference will now be made in detail to the present preferred embodiments of the invention as described in the accompanying drawings.

FIGS. 1A–1D illustrate the broad range of methods and apparatus embodied in the present invention.

Figure 1A:
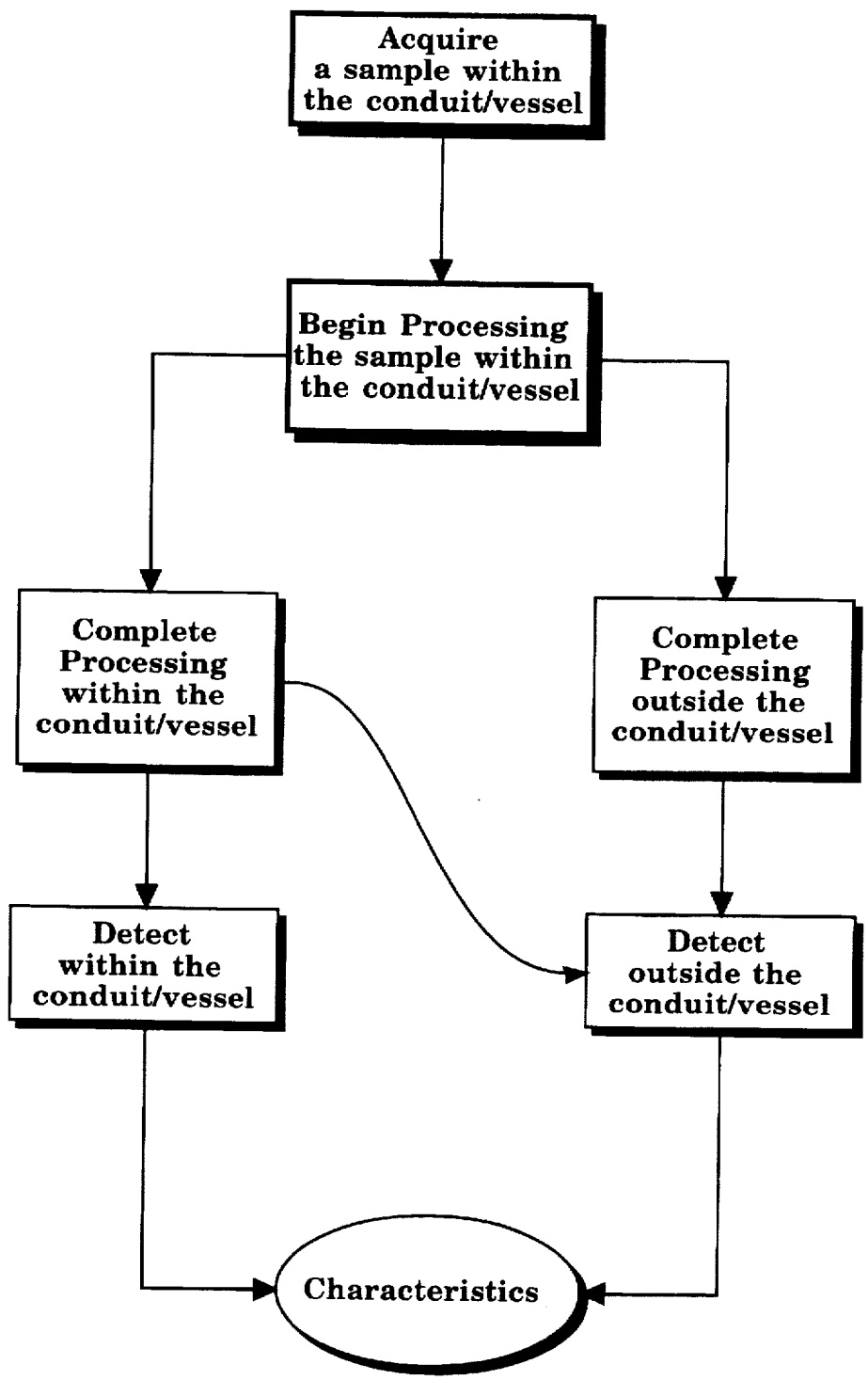
FIGS. 1A, 1B, 1C, and 1D are a series of block diagrams illustrating the method and embodiments of the present invention.
Figure 1B:
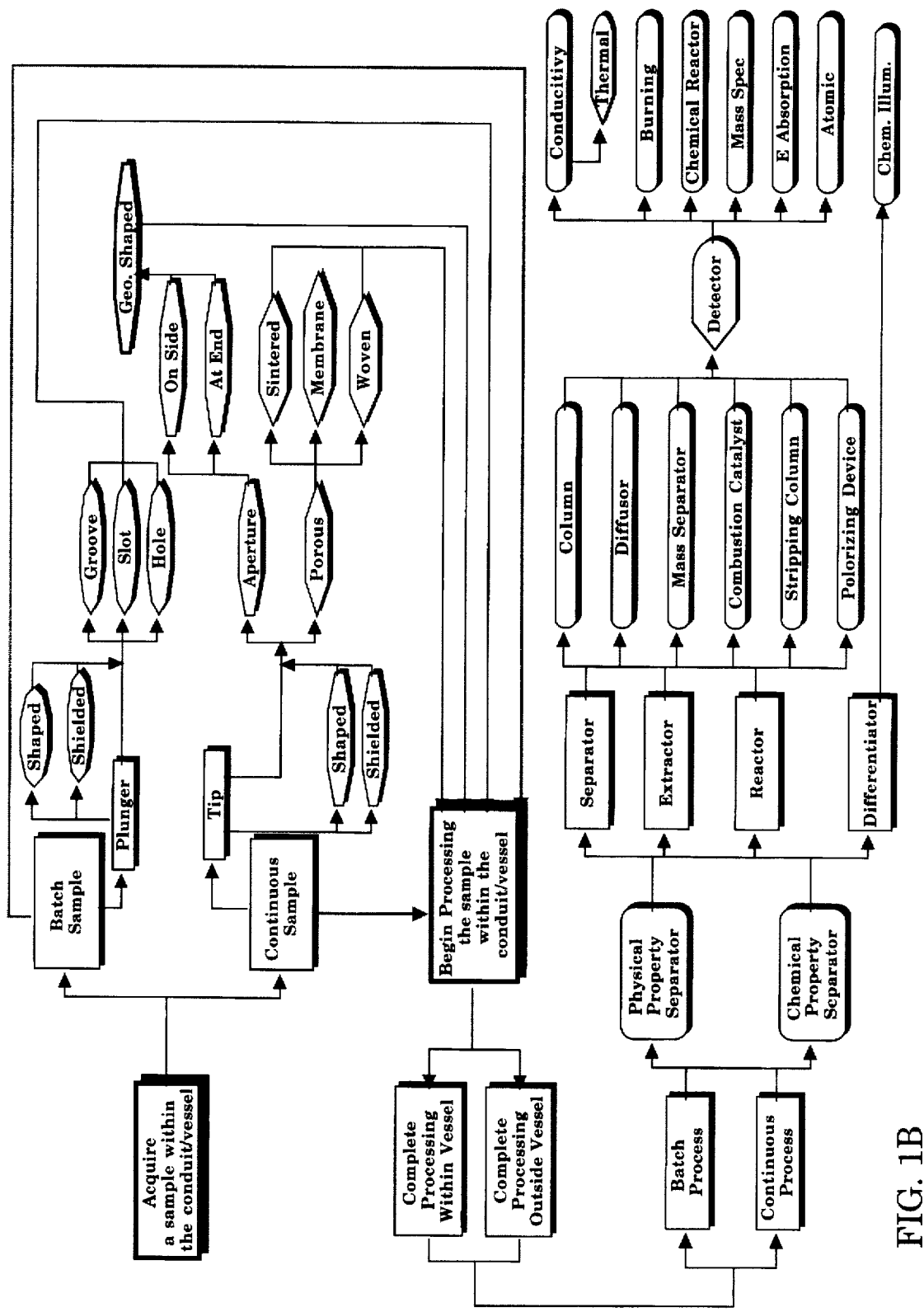
Figure 1C:
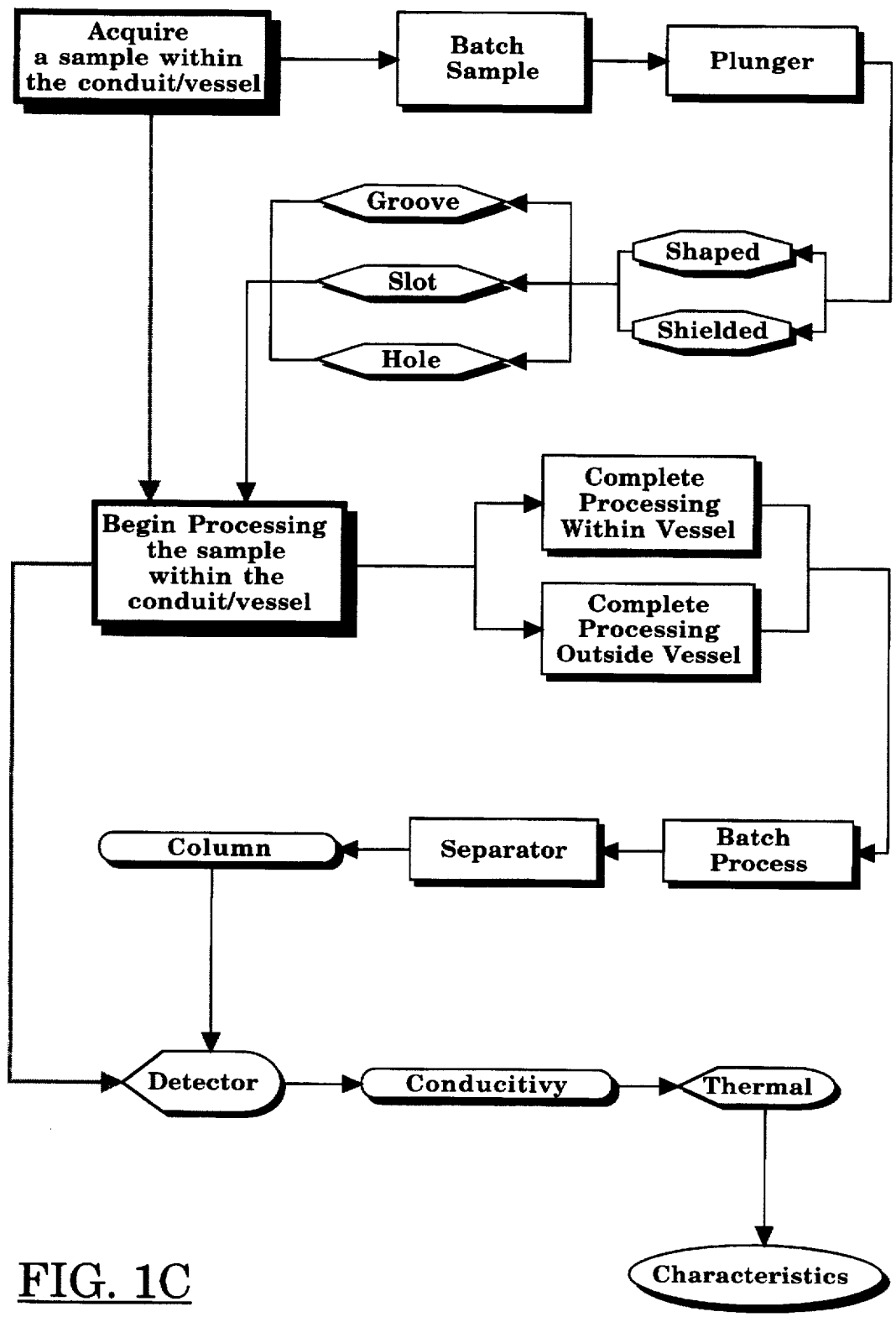
Figure 1D:
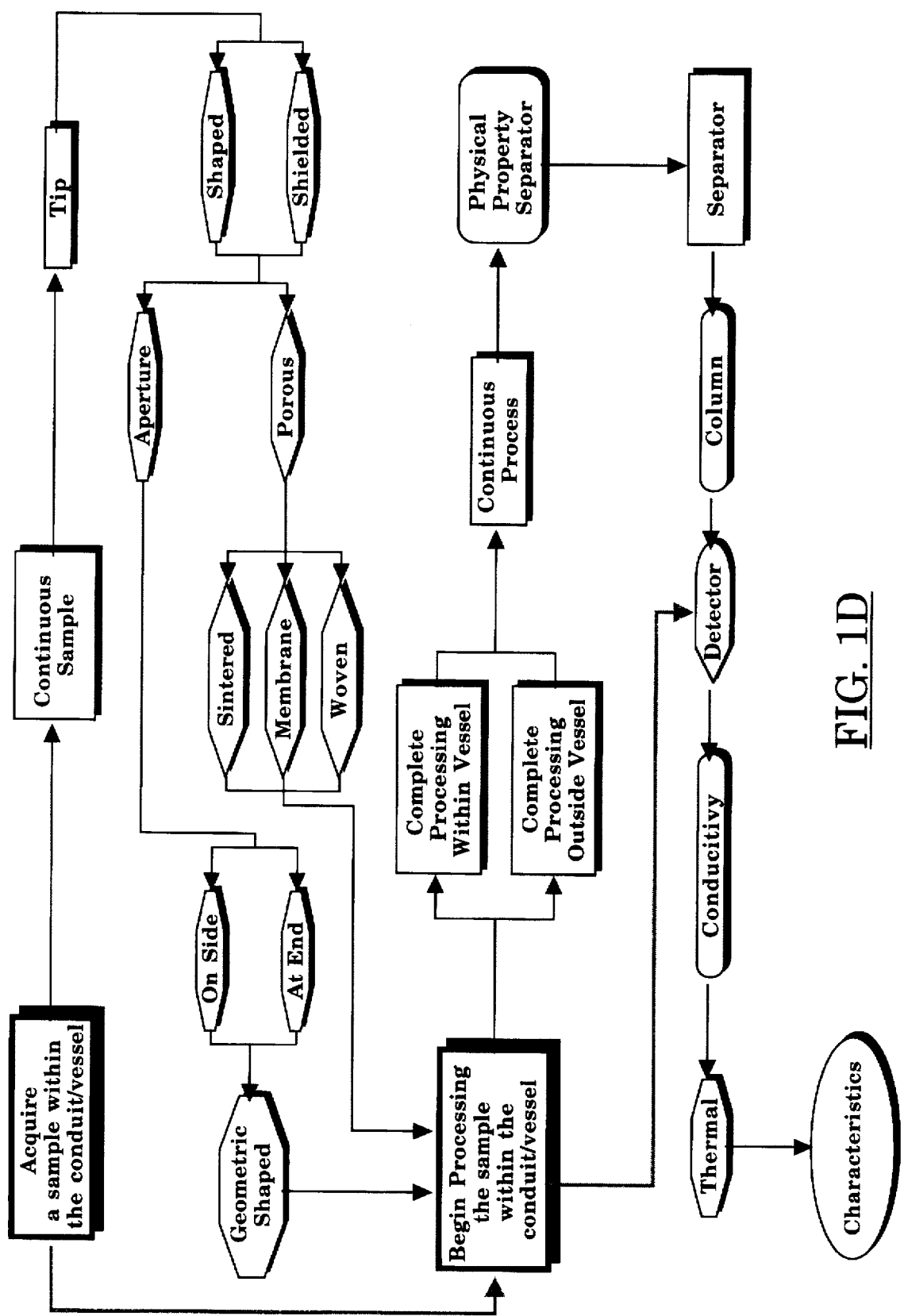

The present invention, as demonstrated in FIG. 1A, provides for acquiring a sample directly from a source, for example, gas from a pipeline, liquid from a vessel or any fluid directly from a conduit. Further, the present invention provides for immediately processing the acquired sample into its components, essentially at the point of acquisition.

Aquisition of the sample can be either a batch or continuous flow into the probe GC.

A batch sample acquisition system would consist of a means for extracting a small amount of the fluid, gas or liquid, from the stream flow for processing. In a very simple embodiment, the batch acquisition may consist of a direct path to a sample processing valve where the valve operates in a batch mode. In the present embodiment it consists of a plunger or rod which can be extended into the fluid to trap a portion of sample inside a groove, slot or hole in the rod. A groove would usually consist of a channel or depression formed in the circumstance of the rod. The slot may be a slit or notch on the top or side or equivalently, the perimeter, of the rod. A hole may be an opening through the rod in which sample would be trapped when the rod is retracted from the stream.

The plunger may have a unique shape in order to avoid creating a turbulence in the flow or to intentionally promote mixing, prevent clogging, or to facilitate gathering or vaporizing the sample. Similarly, a shield may be placed upstream from the plunger to provide protection from direct contact by particulate matter in the fluid flow. The shield may be partial or full and the shape may vary for the same reasons previously assigned to the plunger.

A continuous sample acquisition system consists of a means for continuously extracting a small amount of the fluid, gas or liquid, from the fluid flow for processing. A continuous sample acquisition system in its simplest embodiment may consist of a straight path through the processing system operating in a continuous mode. In a preferred embodiment, a continuous sample acquisition system consists of a sample tip extending continuously into the flow.

The tip may be geometrically shaped to promote mixing or to avoid turbulence, to prevent clogging or to intentionally define high and low pressure zones. Similarly, a shield may be placed upstream from the sample tip to provide protection from direct contact by particulate matter in the fluid flow. The shield may be partial or full and the shape may vary for the same reasons previously assigned to the tip.

The tip may have an aperture, located somewhere along the body such as the end or side, which may have a special shape to improve the gathering of the sample. The tip may be porous in order to separate the fluids from solids which may clog the system. The porous tip may be a sintered material, a permeable membrane, or a woven material.

The sample processing can be batch or continuous, and utilizes some chemical or physical properties of the sample fluid to yield the necessary conditioning required for the detector to make a quantitative measurement.

The processing method can be separation, reaction, extraction, differentiation, a combination of these, or some other method used to prepare the sample components for measurement. The sample will require processing only to the point of preparing the desired component or components for measurement. This does not mean processing is required for all the components in the sample to be measured.

The separating process is done primarily using physical properties of the sample components in contact with various materials which impart varying types of forces and degrees of force on the different components in the sample. Examples of properties are boiling point, molecular polarization, molecular size, molecular shape, osmotic pressure, mass, etc.

The process of reacting, or processing in a reactor consists of performing a chemical reaction between one or more components in the sample and the reactor device. The chemical reaction can be oxidation by heat combustion, catalytic combustion, catalytic reaction, or some other type of chemical reaction or oxidation.

The process of extraction is generally a separation performed by the addition of one or more components to selectively extract or strip one or more components from the sample. This operation is normally based on certain physical characteristics of some components in the sample fluid such as solubility, vapor pressure, boiling point, or polarization.

In some cases more than one type of processing is done in series to prepare the sample for measurement. One example is a separation done utilizing the boiling point/polarity properties of the components in the sample and then passing all or part of the components through a catalytic and/or oxidation combustion device to react and further prepare the component/components for measurement.

Another operation of the processing phase is detecting and measuring the components after the sample preparation is complete. Many types of detectors may be used. The detectors are based on measuring some physical, chemical, or atomic property of the components. The detector can be qualitative or quantitative, or a combination of both.

Examples of physical measuring properties are electrical or thermal conductivity, energy absorption, density, and mass. Examples of chemical measuring properties are flame ionization, catalytic chemical reaction, and chemical ionization. Example of atomic measuring properties are atomic radiation and chemillumination.

Figure 2:
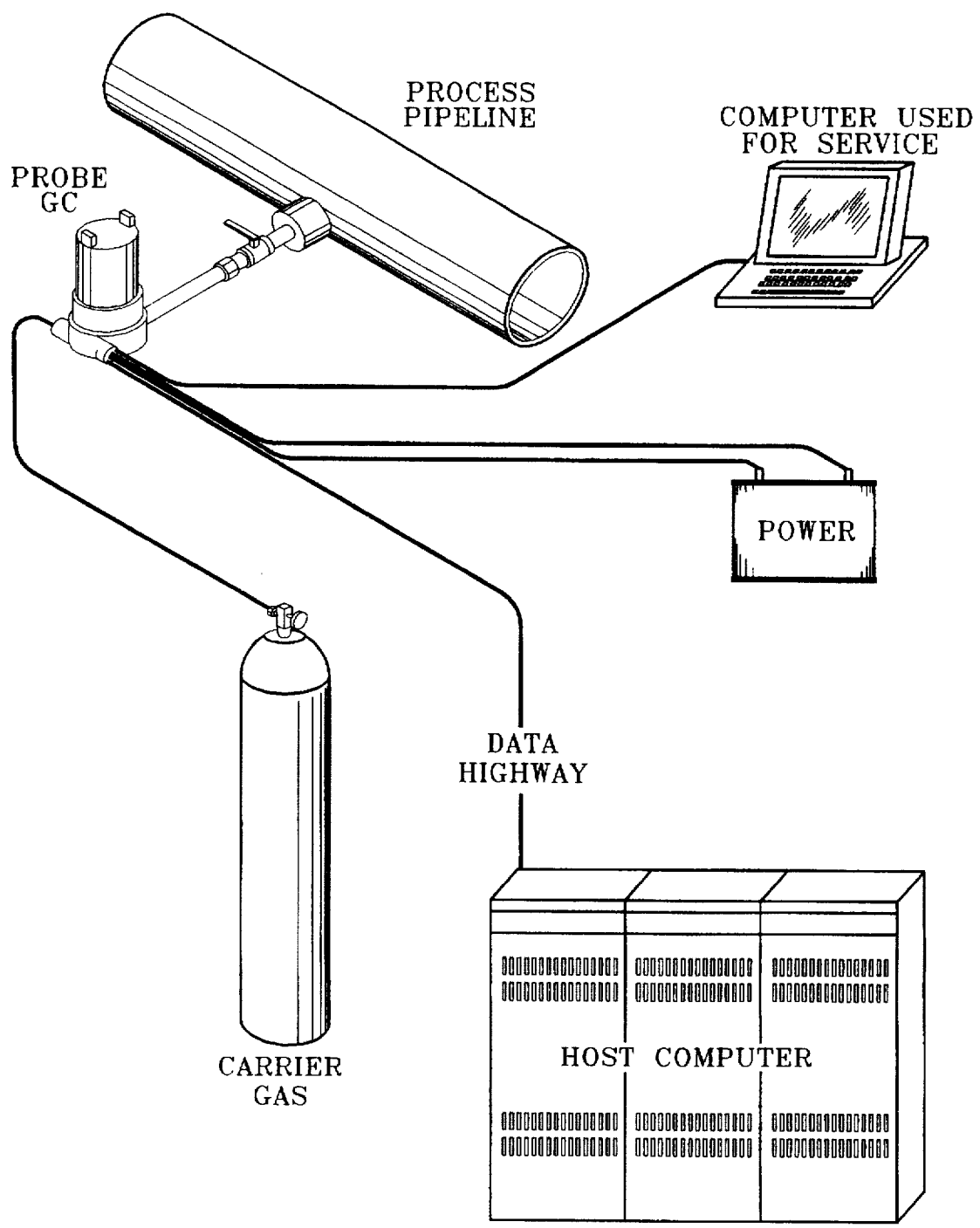
FIG. 2 is perspective illustration of a system depicting the use of the present invention in association with other remote devices connected to a central process controller.

FIG. 2 is a representation of the use of the probe chromatograph with a networked computer system. The only external requirements for the probe chromatograph of the present invention to operate is carrier gas and power. The data may be retrieved several ways and by numerous means in practicing the present invention. For example, the data may be retrieved through a local service computer usually used during maintenance. Also, the data may be retrieved through a data highway to a larger computer. Further, the data may be retrieved through an analog 4–20 mA output used in a local loop to independently control the process.

Still further, the data may be retrieved through a combination of the previously described ways and means as well as other means known to those skilled in the art. Since the probe chromatograph is enclosed in an explosion proof housing and provided proper consideration for installation of wiring and piping, the probe may be interfaced directly with process streams which contain explosive mixtures. For those areas where environmental temperature swings are excessive, a thermally insulative clamshell can be used to enclose the probe housing and electronics conduit.

Figure 3:
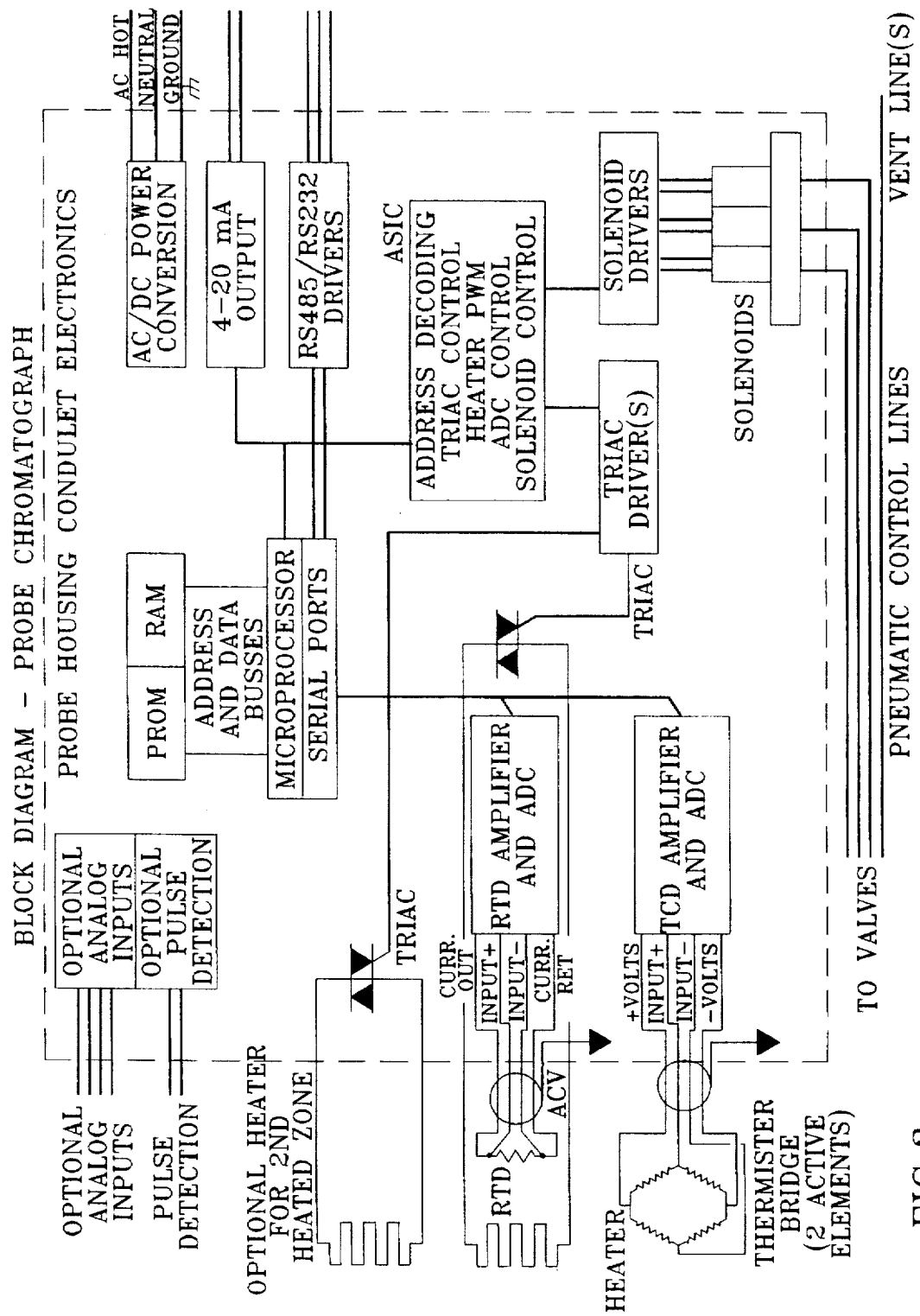
FIG. 3 is a schematic block diaphragm illustrating the electrical components of the probe chromatographic apparatus of the present invention.

FIG. 3 is a schematic block diaphragm illustrating the electrical components of the probe chromatograph of the present invention. The electrical components are physically divided into two zones. The first zone is the chromatograph probe housing or heated zone. The second zone includes the electronics within an explosion proof instrument housing. In a preferred embodiment, the electronics consists of amplifiers, analog-to-digital converters, data ports, heater sense elements, drive elements, and control and decision-making hardware and software. It is known by those skilled in the art of chromatography that different and various electrical component configurations are possible, and indeed available, which configurations are within the scope of the present invention.

Typically, heaters and various sensors are located in the heated zone, although heaters may or may not be used in the preferred embodiment. A microprocessor or other control and decision making hardware and software located in the instrument housing retrieves data from the RTD amplifier and analog to digital converter. The RTD amplifier senses the temperature of a heater used to maintain the chromatograph columns at a constant temperature. In the presently preferred embodiment, triacs switch an AC line to the heater elements for a duration of time proportional to the heat required. Since the probe chromatograph of the present invention is installed directly into the process fluid to be measured, in many cases it will already be at an optimal temperature for measurement and little or no heating will be required. In other cases and particularly, for example, with liquid sampling, the column temperature will be controlled. Further, an additional heated zone may be required. The heated zone may be used, for example, to vaporize liquid. As long as the temperature is always sufficient to vaporize the liquid, feedback control is not necessary.

In a preferred embodiment, the temperature differential is measured using a bridge with two active elements. These active elements are thermister beads: one inserted in the pure carrier gas used as a reference and the other inserted in the carrier gas mixed with the sample gas. The difference is measured using a differential amplifier coupled to an analog-to-digital converter. In a preferred embodiment, the digital data from the converter is serially linked to a microprocessor or other control and decision making hardware and software. After operating on the data, the microprocessor will typically send the data to a host system (see FIG. 2) via one of several optional serial link configurations.

In a preferred embodiment, electrical solenoids switch actuation gases which in turn switch other valves within the probe assembly. The solenoids are driven by a two stage process. Initially a pulse is applied to the solenoid of sufficient duration to turn it on. Afterwards, a pulse width modulated pulse train is applied to hold the solenoid on. The duty cycle of the pulse train is adjusted to guarantee operation over the entire environmental range. The frequency of the pulse train is selected so that the solenoid inductance integrates the current such that the frequency component is averaged to the dc value of the holding current.

With the addition of detection circuitry, usually magnetic, to detect the rotation of a flow turbine blade, flow calculations could be made and a total energy measurement determined. Alternatively, with the addition of two more analog channels a differential pressure measurement could be made which could be converted to an estimated flow rate again facilitating a total energy measurement past a point in the vessel or conduit.

Optionally, in other embodiments, sensors and electronics may be split in different schemes, such as smart sensors where control and/or decision electronics are integrated with the sensor and located remotely from the other electronics.

Figure 4:
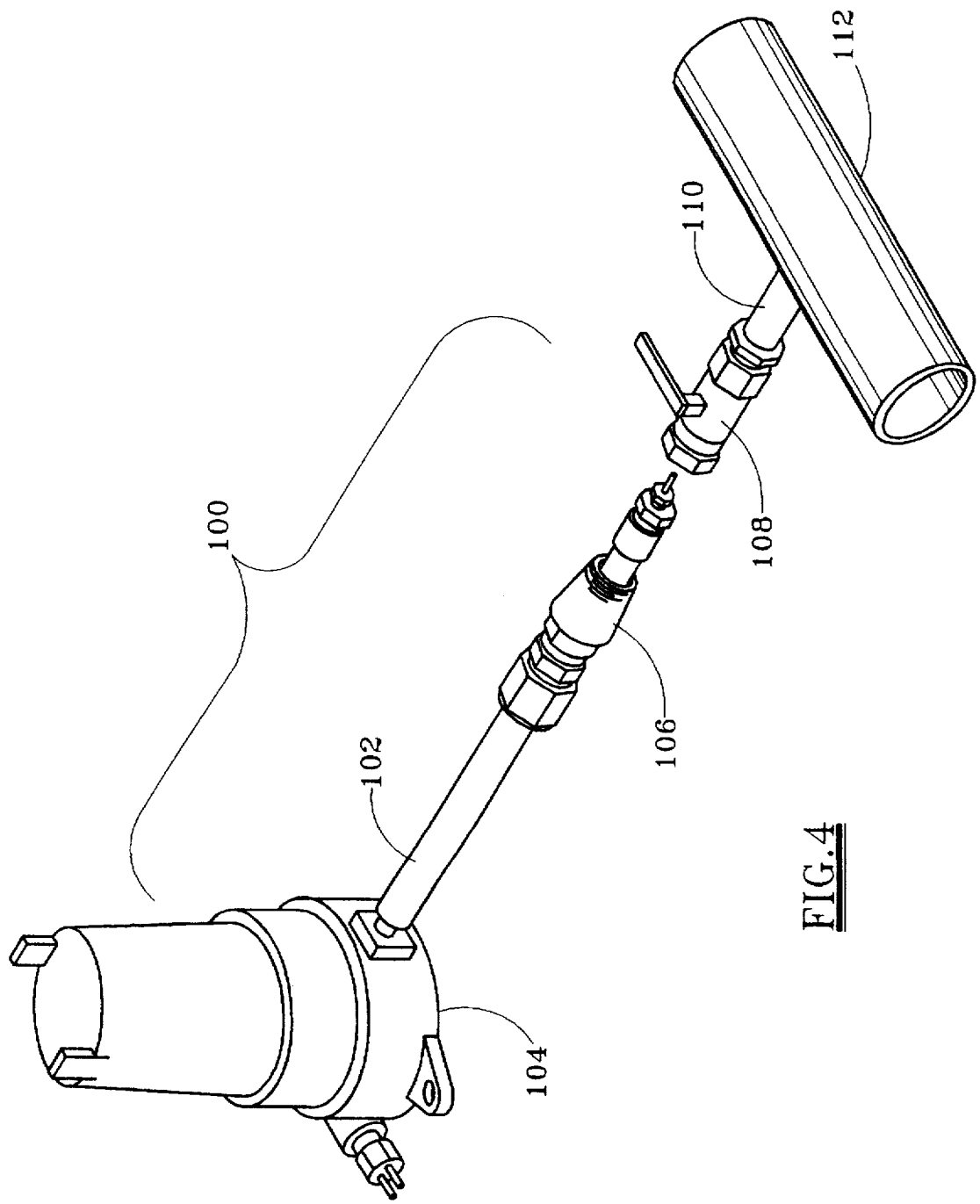
FIG. 4 is a perspective, exploded view of one embodiment of the probe chromatographic apparatus of the present invention interfacing into a process line or vessel.

FIG. 4 is a perspective, exploded view of one embodiment of the probe chromatographic apparatus of the present invention interfacing into a process line or vessel. FIG. 4 illustrates the probe chromatographic assembly 100, including a probe housing 102 and an instrument housing 104. The probe housing 102 is removably associated with the instrument housing 104. The probe housing 102 extends through and is removably associated with the packing gland housing 106. The packing gland housing 106 securedly engages a ball valve 108. The ball valve 108 is fixedly secured to a pipe nipple 110. The pipe nipple 110 is fixedly secured by, for example, welding to a process pipe or vessel 112 (see FIG. 7).

The probe GC assembly 100 can be easily inserted through the ball valve 108 for engaging the sample tip associated with the probe chromatographic assembly 100 into the flow stream. The packing gland housing 106 can be disengaged from the ball valve 108 such that the probe chromatographic assembly 100 is removed from engagement with the pipe nipple 110 and removed from the flow of fluid in the process pipe or vessel 112. FIG. 4 also illustrates the use of a flexible cable to provide power, carrier gas and calibration gas to the probe 100.

Engaging the sample tip directly with the fluid flow provides for enhanced characteristics associated with the probe chromatograph 100 of the present invention. The sample is taken directly from the process flow, without a sample conditioning system. Taking samples directly from the process flow stream, with minimum conditioning of the sample, requires that the process flow be relatively free of sludge or particulate matter which may clog the probe tip or sample valve. Requiring that the process flow be relatively free of sludge or particulate matter may limit specific applications to streams which are generally considered "clean." However, the present invention can be modified by those skilled in the art to include cleaning streams without avoiding the scope of the present invention. For example for streams which may clog the tip, sample conditioning can be added. Preferably, the probe assembly is in intimate contact with the process fluid, but such a requirement is not mandatory in practicing the present invention.

FIG. 5 is a schematic flow diagram showing examples of sample fluid and carrier gas paths associated with the preferred valves inside the probe chromatographic apparatus of the present invention. FIG. 5 illustrates the sample fluid and the carrier gas flow paths in both the purge configuration and the sample inject configuration. The principle of process chromatography as applied to the probe chromatograph 100 is the continuous flowing of the sample fluid through the sample loop 1 and 4 of the sample valve 400B, and the flowing of the carrier gas through the sample valve 400B by the pass ports 5, 6, the column switch valve 400C, the columns, and the detector. In the sample inject configuration, the column switch valve 400C is switched to change the flow path of the carrier gas through the column 501, and the sample valve 400B is switched to transfer a fixed sample loop volume of the sample fluid from the sample flow path into the carrier gas flow path. The small fixed volume of sample is carried by the carrier gas through the columns for component separation and to the detector for quantitative measurement.

As illustrated in FIG. 5, the carrier gas is branched into three separate flow paths. The carrier gas source is pressure controlled with a precision pressure regulator. The control pressure is determined by the chromatographic application or analysis required, and the columns 501, 502 selected to do the component separation. The columns 501, 502 may be changed or alternately used for different applications. The diameter, the length and the type of column determines the amount of carrier gas pressure required.

In the preferred embodiment, the restrictors $R_1$, $R_2$, $R_3$ are capillary tubes sized to give the desired flow rate or pressure drop for the control pressure selected. Equivalently, the restrictors $R_1$, $R_2$, $R_3$ can be adjustable needle valves. The restrictor $R_3$ determines the flowrate to the detector reference sensor. The restrictor $R_1$ is sized to duplicate the pressure drop of the column 501. The restrictor $R_2$ is used to duplicate the pressure drop of column 502. In the sample inject configuration columns 501 and 502 are aligned in series in one flow path to the detector. The restrictors $R_1$, $R_2$ are in series in the other flow path to vent. In the purge configuration, the column 501 and the restrictor $R_2$ are in series to vent, and the restrictor $R_1$ and the column 502 are in series to the detector. In the purge flow configuration when $R_2$ is aligned with the column 501, the carrier gas flow direction is reversed through the column. Reversing the flow direction purges the column 501 to prevent heavy components in the sample from building up and contaminating the column. In this manner, the column 501 protects the main separating column 502 from heavy component contamination.

The valves 400A, 400B and 400C are 6 ported switching valves. The internal flow paths are changed by switching gas pressure to the respective operating ports. When operating gas pressure is applied, the path is blocked. When gas pressure is removed, the path is open. In the valves 400B and 400C, there are two sets of three blocking pistons that operate in unison. In the valve 400A, there are four blocking pistons. The ports 1–6–5 operate in unison, and the ports 2–3 and 3–4 operate independent of each other. The different flow paths are shown in the two configurations of FIG. 5.

FIG. 5 illustrates that the sample valve 400B as designed for a gas sample. Also, FIG. 5 includes a sample block valve 400A used to equilibrate the sample in the sample loop to atmospheric pressure to insure a constant quantity of sample in the fixed sample loop volume. The sample flow path is through the sample probe to the port 2 of the valve 400A, the exit port 3, to the port 3 of the valve 400B, through the sample loop ports 4, 1, the exit port 2, to the port 6 of the valve 400A, and the exit port 1 to the sample return line. Before valve 400B is switched to inject the sample, valve 400A is switched to block the sample flow from port 2 to port 3 and from port 6 to port 1 and opening the path from port 6 to port 5 allowing the sample trapped in the sample loop to depressure to atmospheric pressure. After sufficient time for the sample to equilibrate to atmospheric pressure, the valve 400B is switched to divert the carrier gas flow through the sample loop to carry the trapped sample to the valve 400C, the port 3, and the exit port 2 to the column 501. The flow path is illustrated in the sample inject configuration of FIG. 5.

The components to be measured are separated from the heavy components of the sample by the column 501. The components to be measured are carried into the column 502 for further separation. The valve 400C is switched to the purge configuration which reverses the carrier gas flow in the column 501 to back-purge the heavy components to the vent, but continues the carrier gas flow in the column 502 in the same direction to complete the component separation and transport the flow to the detector.

FIG. 6 is a schematic flow diagram showing different sampling technique along with the carrier gas paths associated with the preferred valves inside the probe chromatographic apparatus of the present invention. FIG. 6 illustrates the purge and sample inject configurations for a different type of sample valve. The valve is used primarily for sampling a liquid fluid, but can be used for gas fluids. The carrier gas flow paths for the columns and restrictors and the chromatographic analysis operation is the same as described for FIG. 5. With liquid fluids, the sample is not compressible, therefore, the sample block valve 400A is not required.

The sample valve 1300 is designed with a piston operated sliding rod or plunger with a cavity configured as a groove, slot, or hole (refer to FIG. 13 detail A, B, and C) for holding a small quantity of sample. The cavity is moved into the process sample fluid and allowed to fill. Then, the rod or plunger is retracted moving the cavity filled with sample into a heated (if heat is required) carrier gas path. The sample is vaporized and is carried via the carrier gas through the same analysis procedure as described for the columns and restrictors in FIG. 5.

The probe chromatograph 100 has the enhanced feature of low or zero environmental pollution from the sample. In FIG. 5, the sample flow is less than 10 cc per minute because of the short distance from the process fluid to the sample inject valve. In FIG. 6, the sample flow is zero because of the sample transfer feature of the sample valve.

Figures 7, 7A:
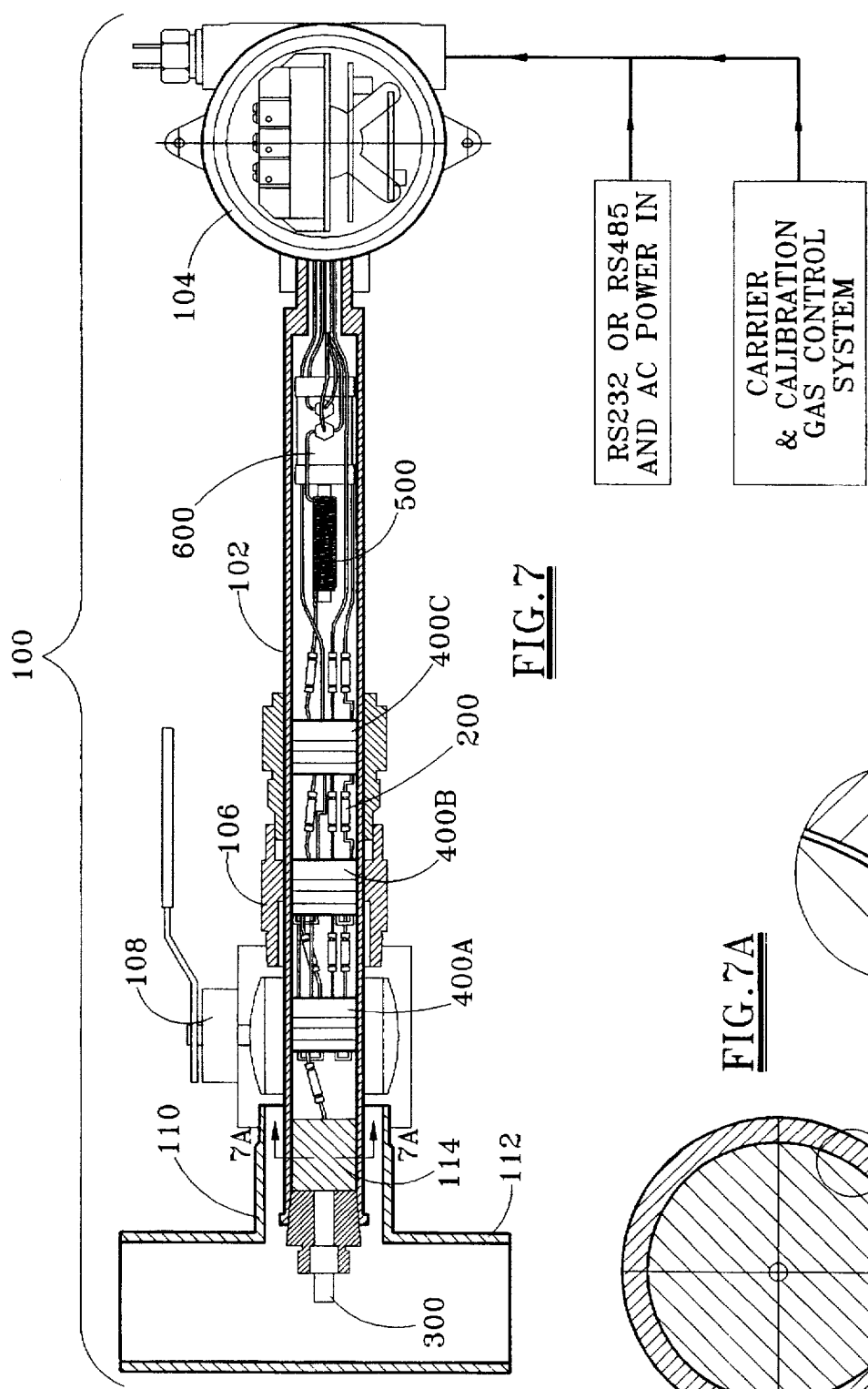
FIG. 7 is a partial, cross-sectional view of the probe chromatographic apparatus of the present invention for use in sampling vapor process fluids.
FIG. 7A is a cross-sectional view, and associated blow-up, of the probe chromatographic apparatus of the present invention taken along the section A—A of FIG. 7 illustrating one embodiment of the flame path and associated plug of the present with an exploded view illustrating the flame path in FIG. 7A.

FIG. 7 is a partial, cross-sectional view of the probe chromatograph assembly 100 of the present invention for use in sampling vapor process fluids. The probe chromatograph assembly 100 is illustrated engaged with a process pipe or vessel 112. The probe chromatograph assembly 100 is directly in the fluid flow passing through the pipe 112. The probe housing 102 is secured by a ball valve 108 in association with a pipe nipple 110.

The probe housing 102 aligns a sampler assembly 300 to be placed into the fluid flow path with the sample hole opening downstream to keep particulates out of the sample tip that is passing through the pipe 112. The primary components of the probe 100 are the sample assembly 300, one or more valves 400, connecting tubing and unions 200, a chromatographic separating column assembly 500, a detector 600, an instrument housing 104, one or more solenoid valves, PC boards, one or more vent ports, an AC power supply and a carrier and calibration gas control system with associated wires and tubing.

The chromatograph components are installed inside a stainless steel probe and the control electronics are installed inside an explosion-proof condulet attached to the probe. All the tubing in or out of the explosion-proof condulet are sized to constitute a flame proof path. All the connecting wiring is run through a National Electrical Code (NEC) approved seal. The end of the chromatograph probe inserted into the process vessel includes a flame path plug 114. The plug is designed to meet the flame arrestor path specifications of the NEC code; that is, a flame path plug which is 1.13 inches long with 0.005 inches maximum clearance between the flame path plug 114 and the internal diameter of the probe housing wall 102. The sample flow tube is installed through a longitudinal hole, through the center of the plug 114, as shown in FIG. 7, with a clearance of no more than 0.005 inches maximum from the wall of the plug to the outside diameter of the tube.

The sample tube in the preferred embodiment is a capillary tube selected to serve as a flame arrester path and to depressure the sample fluid from the process vessel to the chromatographic valves 400A and 400B. The capillary sample tube internal diameter and the length selected are based on the process fluid pressure and viscosity and the sample flow desired. The tube internal diameter must be no larger than 0.010 inches or less to meet the NEC flame path specifications. It should be understood that the capillary tube is the preferred embodiment, but other means may be used to reduce the pressure such as a needle valve or a screw path or tapered internal diameter column. All such alternate embodiments are within the scope of the present invention for those skilled in the art.

Figure 8:
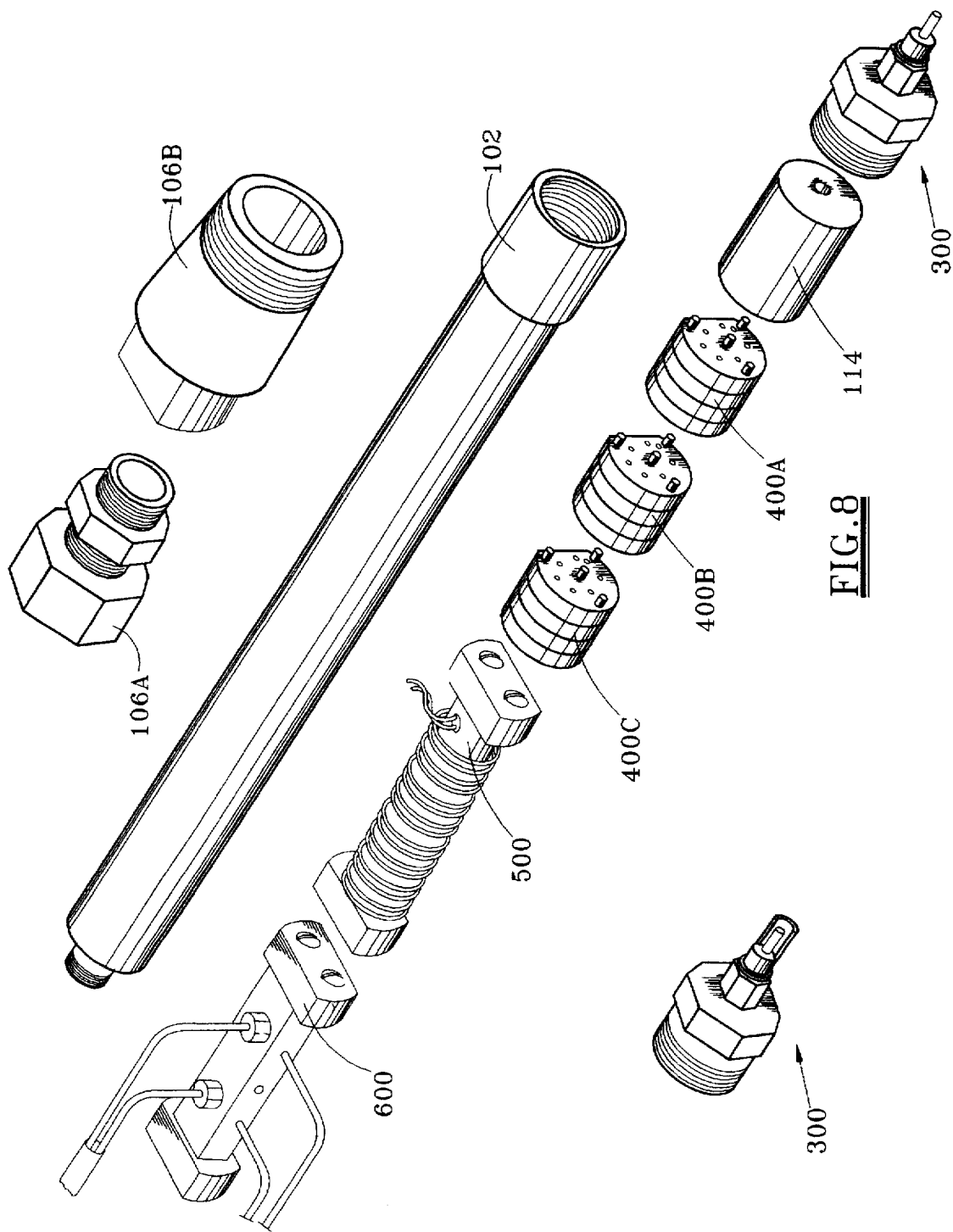
FIG. 8 illustrates an sequential, exploded view of the probe chromatographic apparatus of the present invention for use in sampling vapor process fluids.

FIG. 8 illustrates a sequential, exploded view of the probe chromatographic apparatus of the present invention for use in sampling vapor process fluids. FIG. 8 illustrates an exploded view of the probe chromatograph 100 of the present invention for use in sampling vapor process fluids. FIG. 8 provides a sequential illustration of the primary elements of the probe chromatograph 100 of the present invention as encased in the housing 102 and secured by the packing gland housing assembly 106. The packing gland housing assembly 106 is of known variety and includes a packing gland nut assembly 106A and a packing gland housing 106B. The probe housing 102 provides for securing the relationship between the sample assembly 300, a sample block and calibration valve 400A, a sample valve 400B, a column-switch valve 400C, a separating column assembly 500 and a detector 600.

With reference to FIG. 5, a typical application flow diagram for the three valves, the two separating columns, and the detector are, for example, the following: (a) The pure carrier is flowing through the detector reference sensor to establish a reference condition. (b) The carrier gas is also flowing through and purging the secondary separating column to the detector measuring sensor to establish a zero condition. (c) Via the porting of the valve 400C, the carrier gas flow is divided to flow through the secondary column and to back-flush purge the primary column. (d) The sample fluid is flowing through the tip assembly, the sample block valve, the sample valve, and to the vent.

In preparation for sample injection, the valve 400C is activated and the primary column is switched from the back-flush position to a position in series with the secondary column. The sample block valve 400A is activated to isolate the sample from the process and to equilibrate to atmospheric pressure. The valve 400B is activated and the fixed volume sample is injected into the flowing carrier gas, then returned to the purge position.

A preliminary separation is done on the primary column. As soon as the components to be measured have moved into the secondary column, the primary column is switched back to the purge position for back-flush cleaning. The operation is required to prevent the columns from becoming contaminated with large molecule impurities that may be present in the process fluid.

Figure 9:
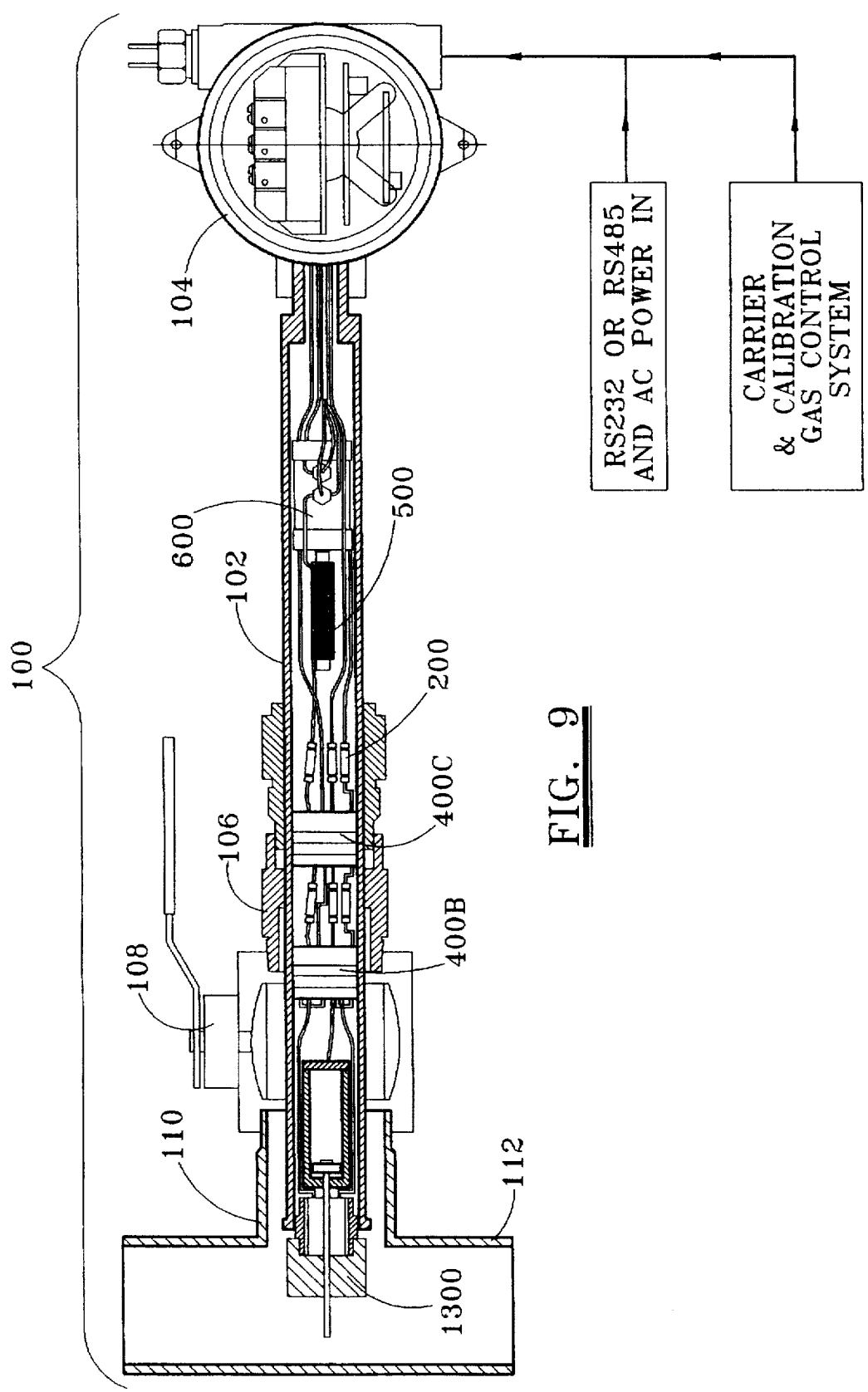
FIG. 9 illustrates a partial, cross-sectional view of the probe chromatographic apparatus of the present invention for use in sampling liquid process fluids.

FIG. 9 illustrates a partial, cross-sectional view of the probe chromatograph 1000 of the present invention for use in sampling liquid process fluids. The probe chromatograph 1000 comprises a liquid sampler assembly 1300, a back-flush valve 400B, a column-switch valve 400C, connecting tubing and unions 200, chromatographic separating columns 501 and 502, a detector 600 and an instrument housing 104 and associated components. The components are encased in the housing 102. The housing 102 is engaged with the packing gland 106, the ball valve 108 and the pipe nipple 110. The housing 102 provides that the liquid sampler assembly 1300 is affixed flush with the wall of the pipe 112. The sampler assembly 1300, for liquid or gas samples, is designed such that there is no direct flame path between the process fluid and the inside of the probe chromatograph 1000.

FIG. 9 illustrates a partial, cross-sectional view of the probe chromatographic apparatus of the present invention for use in sampling liquid process fluids. The view provided in FIG. 9 is with the rod extending from the liquid sampler assembly 1300 into the fluid flow to illustrate the purge mode of the liquid sampler assembly 1300.

Figure 10:
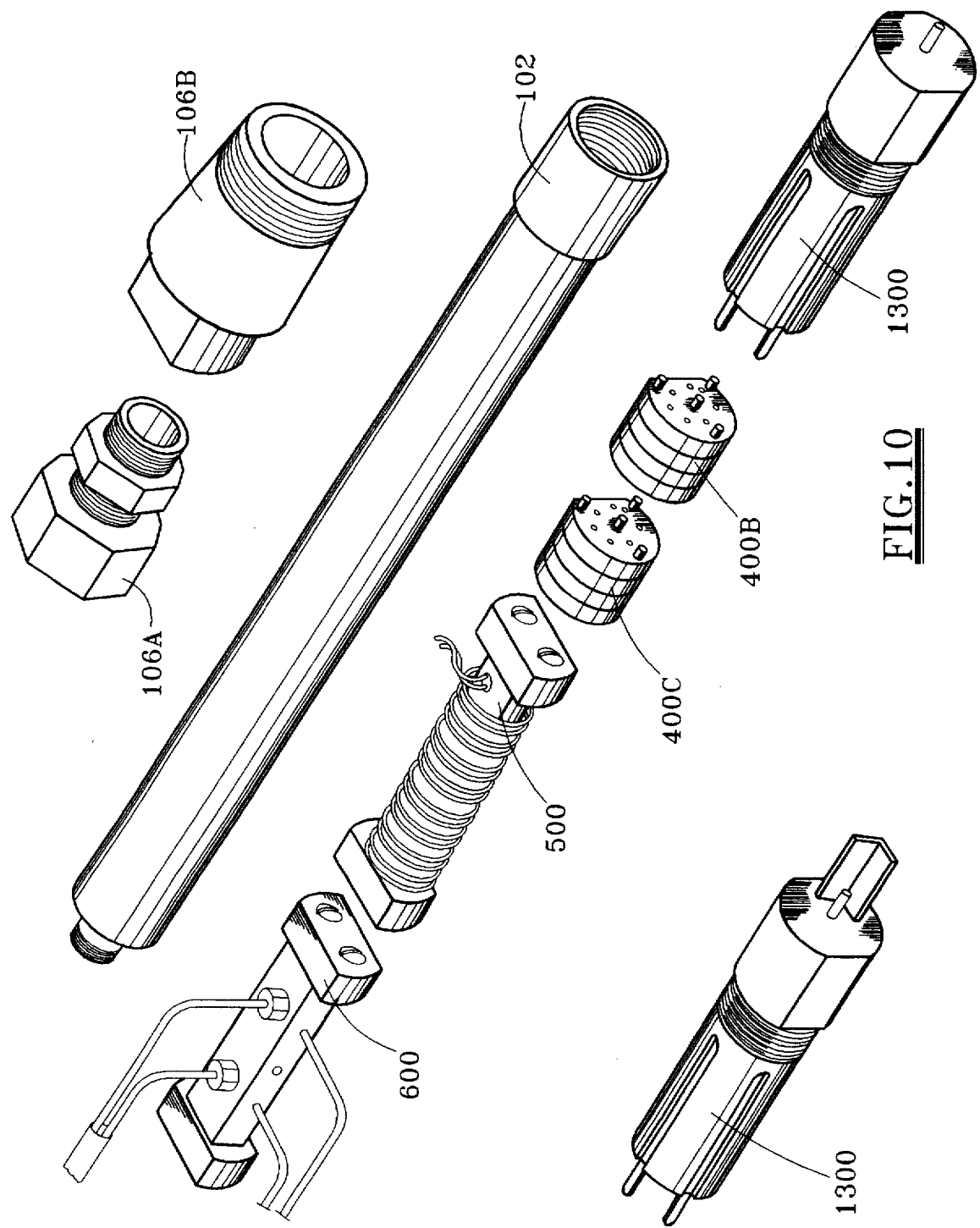
FIG. 10 illustrates a sequential, exploded view of the probe chromatographic apparatus of the present invention for use in sampling liquid process fluids.

FIG. 10 illustrates a sequential, exploded view of the probe chromatographic apparatus of the present invention for use in sampling liquid process fluids. FIG. 10 provides a sequential illustration of the primary elements of the probe chromatograph 1000 of the present invention as encased in the housing 102 and secured by the packing gland housing assembly 106. The packing gland housing assembly 106 includes a packing gland nut assembly 106A and a packing gland housing 106B. The probe housing 102 provides for securing the connection between the sample assembly 1300, the back-flush valve 400B, the column-switch valve 400C, the separating columns 501 and 502, and a detector 600. The column-switch valve 400C is performing the same function as the valve 400C in FIG. 6. The flow diagram is configured and the valves tubed to perform various and different types of sample component separations depending on the desired analysis, or the components of the sample to be measured.

In the purge position, the carrier gas flow diagram is basically the same as the flow diagram for the vapor sample. The difference is the way that the sample fluid is measured and injected into the carrier gas flow path. The liquid sample valve has a rod or plunger which may be shielded from the flow or bare (refer to FIG. 10, detail A and B) with a groove, slot or hole that extends into the process fluid. The sample valve 1300 is switched to capture a precise volume of the sample. The liquid sample rod or plunger pulls a predetermined amount of liquid sample into its heated zone, where it is vaporized so that the carrier gas can sweep the sample from the liquid sample valve 1300 to the column 501. One or more columns may be appropriately used depending on the analysis required. The back-flush valve 400B can be used to back flush column 501 to vent or directly into the detector 600. The column-switch valve 400C can be activated to allow components to be cut from the detector 600 as appropriately needed. Thus, eluants of differing molecular structure can be measured using the probe 1000 of the present invention without contaminating the columns 501 and 502 due to large molecular impurities.

FIG. 11 is a break-away perspective illustration of a capillary sampler assembly 300 as taught by the present invention. It can be appreciated that the sample assembly 300 can have numerous configurations adaptable for use with the probe chromatograph 100 of the present invention. The sampler assembly 300 illustrated in FIG. 11 includes a connector 302, a tubing 312, and a nut member 304. The sample member stop 314, a stem 116 and an opening 318. Opening 318 can be to the side as illustrated in detail A or open to the end as illustrated in detail B of FIG. 11. The sample member stop 314 is secured into position between the connector 302 and the nut member 304. The stem 116 protrudes through the hole in the nut member 304 so as to be placed into the fluid flow as illustrated in FIG. 7. FIG. 11 illustrates that the opening 318 is provided to connect with the tubing 312 such that a sample taken into the opening 318 passes through the stem 116, through the sample member stop 114 and through the tubing 312 into the tubing and unions 200 within the probe housing 102 (See FIG. 7).

FIG. 12 is a break-away perspective illustration of another embodiment of a sampler tip assembly 300 using a porous sample tip as taught by the present invention. The porous sample tip assembly can be constructed of a sintered material, a porous membrane or a woven material. A sample member stop 324 uses a porous stem 326. The sample member 324 is engaged between the connector 302 and the nut member 304 such that the sample member stop 324 securely engages the connector 302 and the nut member 304. The porous stem 326 extends through the hole in the end of the nut member 304 to be placed into the fluid flow in the pipe 112 as illustrated in FIG. 7. The porous stem 326 can provide for omni-directional sampling within the fluid flow.

FIG. 13 is a break-away illustration of the liquid sampler assembly 1300. The liquid sampler assembly 1300 comprises a housing 1302, a cap 1304 having an aperture 1304A through which a rod or plunger 1310 can protrude. The rod 1310 has a groove, slot or hole 1312 as illustrated in details A, B, or C. The groove, slot or hole 1312 is in channeled communication with a carrier-in channel and a carrier-out channel. A piston 1320 in association with a piston actuator can keep rod or plunger 1310 retracted within the cap 1304 and the casing 1302, or alternately, extend the rod or plunger 1310 through the aperture 1304A and the cap 1304 into the process fluid.

The probe chromatograph of the present invention is adapted for using a heat-sink type system with or without temperature control. The probe chromatograph apparatus of the present invention is adapted to interface directly to the process fluid using liquid sampler assembly 1300. The probe chromatograph of the present invention is designed to directly engage the process sample fluid, rather than bringing the process sample fluid to the chromatograph. The probe chromatograph of the present invention does not use a conventional sample conditioning system since the probe chromatograph is directly engaged with the process fluid being analyzed.

Temperature control is not critical for use with the present invention because the electronic control unit, and associated microcomputer, can compensate for detector drift and small peak elution time changes. Elution time compensation is achieved by identifying the components in the process fluid and exchanging the retention times from the previous run with the retention times of the present run. As long as the components do not swap elution positions, this technique is applicable. Detector drift is corrected when calculating peak areas by detecting the baseline at the beginning and the end of a peak. For the purpose of integrating the area under the peak, the beginning and ending points are connected to form a base line. If the detector drifts upward or downward monotonically during the peak, the effects will be approximately corrected by a change in the slope of the baseline.

Figure 15:
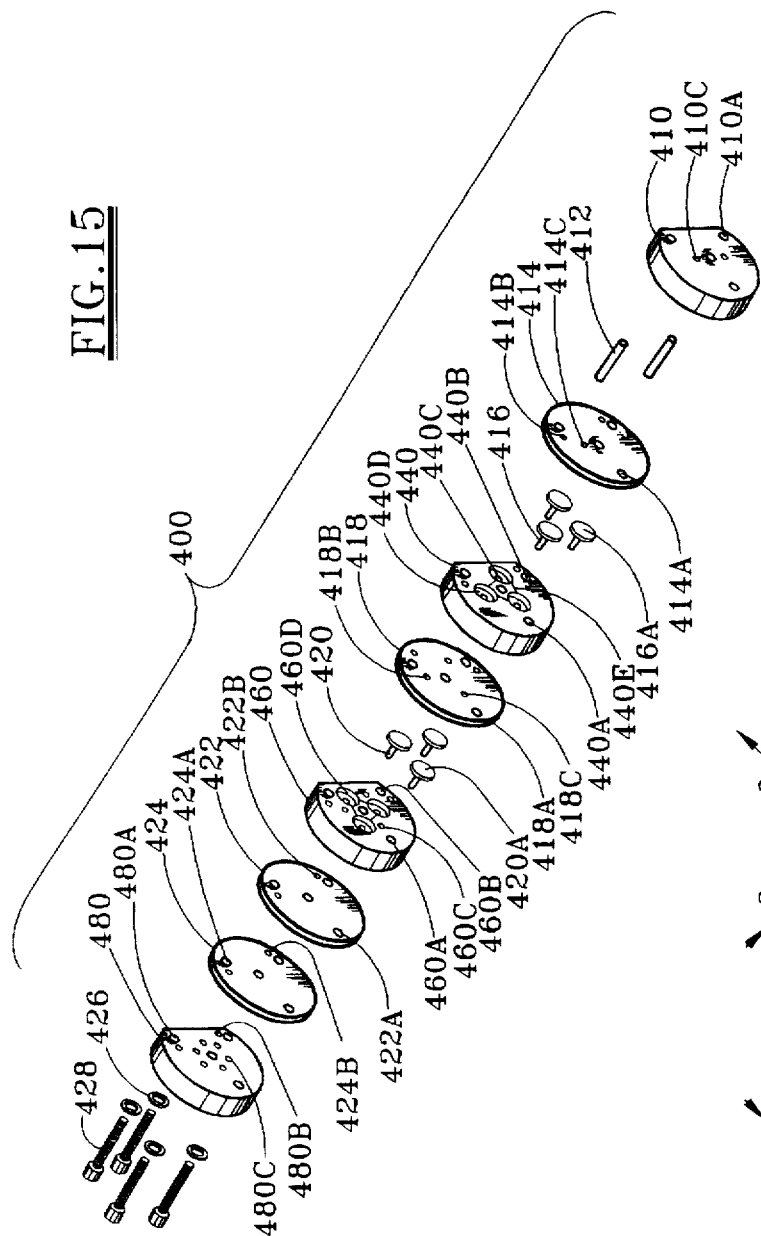
FIG. 15 is an exploded view from the opposite direction of the multi-port mini-valve illustrated in FIG. 14.

FIG. 14 is an exploded view of a multi-port mini-valve as taught by the present invention. FIG. 15 is an exploded view from the opposite direction of the multi-port mini-valve illustrated in FIG. 14. FIGS. 14 and 15 illustrate exploded views from different directions, of a multi-port mini-valve 400 as used in the present invention, the preferred multi-port mini-valve 400 used with the present invention is adapted for use with six ports 480C. The basic components of the multi-port mini-valve 400 are a base plate 410, a lower actuator diaphragm 414, one or more long pistons 416, a lower piston plate 440, upper actuator diaphragm 418, one or more short pistons 420, an upper piston plate 460, a cushion diaphragm 422, a sealing diaphragm 424 and a primary plate 480. The components for the multi-port mini-valve 400 are held together using one or more guide pins 412, lock washers 426 and screws 428. The guide pins 412 are received by a plurality of holes 480B, 424B, 422B, 460B, 418B, 440B, 414B and 410B. The screws 428 are received by a plurality of holes 480A, 424A, 422A, 460A, 418A, 440A, 414A and 410A.

As illustrated in FIG. 14, the base plate 410 and the lower piston plate 440 have triangular channels 410D and 440D. The triangular channels 410D and 440D are used as manifold ports for piston actuation. The base plate 410 also has two actuation holes 410C, one actuation hole 410C is ported into the triangular channel 410D. When pressure is applied to the actuation hole 410C ported to the triangular channel 410V, the lower actuator diaphragm 414 will flex. The flexing of the lower actuator diaphragm 414 will push the long pistons 416 through the holes 440C in the lower piston plate 440, through the holes 418C in the upper actuator diaphragm 418, and through the holes 460C in the upper piston plate 460, pushing the cushion diaphragm 422 and the sealing diaphragm 424 against the primary plate 480 shutting off flow between the ports 480C as illustrated in FIG. 15, View "A." The other actuation hole 410C is through the base plate 410 and ported into the triangular channel 440D in the lower piston plate 440. When pressure is applied to the actuation hole 410C through the base plate 410 and ported into the triangular channel 440D, the upper actuator diaphragm 418 will flex. The flexing of upper actuator diaphragm 418 will push the short pistons 420 through the holes 460C in the upper piston plate 460, pushing the cushion diaphragm 422 and the sealing diaphragm 424 against primary plate 480 thereby shutting off flow between the ports 480C as illustrated in FIG. 16, View "B."

As illustrated in FIG. 14, the upper piston plate 460 has a groove 460D. The groove 460D allows the cushion diaphragm 422 and the sealing diaphragm 424 to flex into the groove 460D, so that the gases being sampled can flow between the ports 480C in the primary plate 480 as required, when not pushing the cushion diaphragm 422 and the sealing diaphragm 424 with the long pistons 416 or the short pistons 420 against the primary plate 480.

Figure 16A:
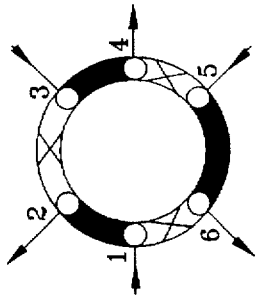
FIG. 16 is a diagram illustrating the operation of a preferred multi-port valve as taught by the present invention including the actuation of long and short pistons associated with the valve and how piston actuation shuts off flow between ports of the multi-port valve.
Figure 16B:
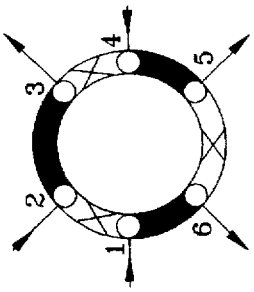

FIG. 16 is a diagram illustrating the operation of a preferred multi-port valve as taught by the present invention including the actuation of long and short pistons associated with the valve and how piston actuation shuts off flow between ports of the multi-port valve. FIG. 16 depicts the actuation of the long pistons shown in view "A" illustrates the shut off of the flow in unison or individually between a first pair of ports 2 and 3, a second pair of ports 4 and 5, and a third pair of ports 6 and 1. When the short pistons are actuated, flow will be shut off in unison or individually between a first pair of ports 1 and 2, a second pair of ports 3 and 4, and a third pair of ports 5 and 6.

FIG. 17 is a break-away perspective view illustrating one embodiment of the separating column assembly 500 of the present invention. FIG. 17 illustrates the columns 501 and 502 being secured between the end plates 514A, 514B using the screws 516A, 516B, respectively. The end plates 514A, 514B are secured to a heat sink 512. The heat sink 512 is drilled for receiving a heater 506 and a heat sensor 508 in the heat sink 512. The columns 501 and 502 can be engaged with the heat sink 512 for providing a stable heating arrangement. In a presently preferred embodiment of the present invention, the columns are used in a helical relationship with the heat sink 512. It can be appreciated that many different sizes and types of columns may be used with the apparatus of the present invention.

FIG. 18 is a break-away perspective view illustrating one embodiment of a detector assembly 600 of the present invention. The primary parts of the detector assembly 600 include a detector block 620 and a thermister 640. The detector block 620 is securely engaged with an end plate 610A, 610B and is held in place using a plurality of screws 612A, 612B. The end plate 610A, 610B securely engages the detector block 620. The detector block 620 has a reference inlet port 652 and a measurement port 654. The reference port 652 is operationally engaged with a thermister 640A. Similarly, the measurement port 654 is operationally associated with a thermister 640B. The thermisters 640A, 640B are securedly engaged with the detector block 620 using a hole 624A, 624B and associated nuts 644A, 644B. Also, a washer 642A, 642B may be adapted for securing the remote ends of the thermister 640A, 640B to appropriately engage the reference port 652 and the measurement port 654, respectively. A cable 646 is used to transfer the signal from the thermisters 640A, 640B.

FIG. 19 illustrates an optional version of the existing embodiment where the probe is housed in a chamber formed in the side of the effluent vessel or conduit. The probe tip may be the retractable plunger type illustrated in FIG. 13 or the fixed tip type illustrated in FIG. 12 or FIG. 13. The tip may be placed in the process stream in such a way as to optimize the measurement while minimizing the possibility of clogging the tip. Access to the inner workings is via a cover housing which forms part of a NEMA 7 explosion proof housing.

FIG. 20 illustrate optional embodiments which have effluent flowing on all sides. The electronics can be inside the streamlined housing or alternatively mounted on the outer wall of the vessel or conduit.

FIG. 21B illustrates optional embodiments of FIG. 20 except the shape of the chromatograph system is intentionally chosen to create a differential pressure drop in the fluid across the device. By knowing the relationship between the pressure drop and the flow of effluent, a flow can be calculated and once again, a total energy measurement can be made. Gas tubes and signals could exit via the supports which may be affixed in the conduit or vessel by some fastener means. Optionally, the geometry of the probe tip can be shaped to create a pressure differential as illustrated in FIG. 21A. When a fluid sample is being taken, pressure measurements are not being made.

Figure 22A:
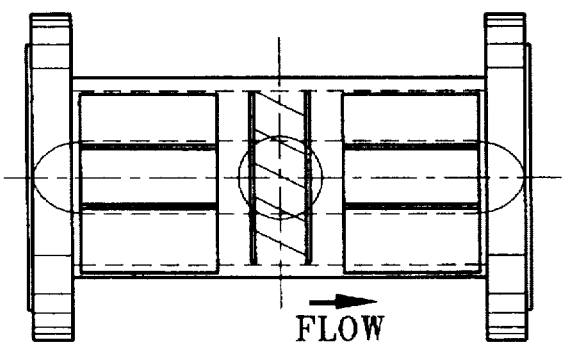
FIGS. 22A, 22B AND 22C illustrate an optional embodiment of the present invention as shown in FIG. 20, but incorporating a flow straightener of a turbine device used to compute fluid flow and total energy measurement.
Figure 22B:
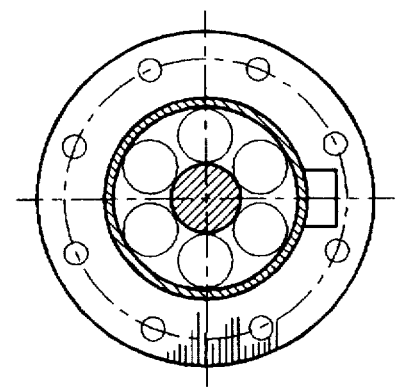
Figure 22C:
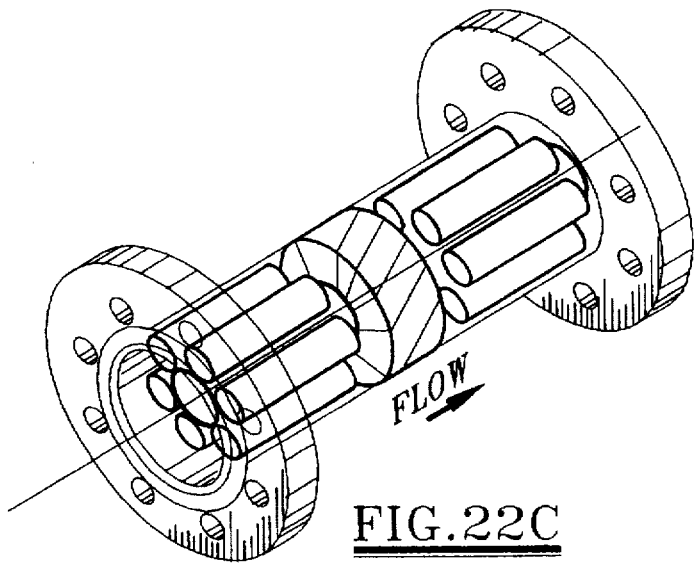

FIGS. 22A, 22B, and 22C illustrate that with the addition of a blade turbine and flow straighteners, the chromatograph can contain the axle shaft for the flow meter. The shape of the flow straighteners and affixing methods can vary as required by design. For instance if the probe is shaped to form a nose cone for the flow turbine, upstream and downstream forces on the rotor can be balanced to improve the linearity of the device. The combination of a flow measuring device and a chromatograph system for measuring energy content of a sample of gas can be used to measure total energy passing a point in the conduit.

Figure 23:
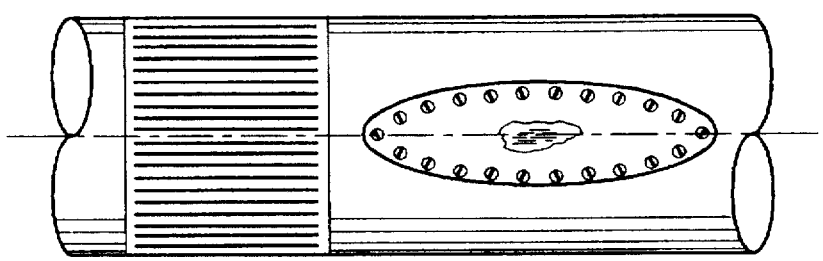
FIG. 23 illustrates an optional embodiment of the probe with an external solar array and optical interface to maintain intrinsically safe operation.

FIG. 23 illustrates a method of providing energy to the chromatograph located within the process vessel or conduit via an amorphous solar array, for instance, which could be made intrinsically safe. A fiber optic connector or the like could be used to transmit data from the hazardous location to the safe area.

Additional advantages and modifications will readily occur to those skilled in the art. The invention in its broader aspects is therefore not limited to the specific details, representative apparatus, and the illustrative examples shown and described herein. Accordingly, the departures may be made from the details without departing from the spirit or scope of the disclosed general inventive concept.

What is claimed is:

1. A probe for making chromatographic measurements at the location of sampling of a fluid, rather than at a remote location, to obtain information concerning one or more components of the fluid wherein the fluid is in a conduit, vessel or reactor, the probe comprising:

(a) a housing having a first end, the housing attached to the conduit for extending the first end of the housing into the conduit with the fluid, (b) a sampler affixed within the housing such that a portion thereof extends from the first end of the housing into the conduit, the sampler for acquiring a sample from the fluid in the conduit such that the sampler is in the fluid in the conduit, (c) a processor for receiving the acquired sample from the sampler and for initiating processing of the acquired sample within the housing such that the processor is in the housing in the fluid inside the conduit, (d) a separator for accepting the processed sample from the processor and for separating the processed sample into respective components such that the separator is in the housing, and (e) a detector for accepting the separated components of the processed sample and for analyzing the separated components to obtain information concerning one or more components of the fluid such that the detector is in the housing whereby the probe is affixed to the conduit.

2. The probe chromatograph as defined in claim 1 further comprising a controlled flame path within the probe separating the vessel from combustion within the probe.

3. The probe chromatograph as defined in claim 1 wherein the sampler promptly provides the processor a sample of predetermined volume.

4. The probe chromatograph as defined in claim 1 further comprising means for removing suspended particulate matter from the fluid.

5. The probe chromatograph as defined in claim 1 further comprising an explosion proof containment in the probe housing.

6. The probe chromatograph as defined in claim 1 further comprising an enclosure for containing the probe within the vessel.

7. The probe chromatograph as defined in claim 1 further comprising a flow measuring device for determining the total energy transfer within the vessel.

8. A method for making chromatographic measurements at the location of sampling of a fluid, rather than at a remote location, to obtain information concerning one or more components of the fluid wherein the fluid is in a conduit, vessel or reactor and the method effected in a probe comprising a housing having a first end, the housing attached to the conduit for extending the first end of the housing into the conduit with the fluid, the method comprising the steps of:

(a) acquiring a sample from the fluid in the conduit such that the sample ingresses the first end of the housing extending into the conduit, (b) receiving the acquired sample for initiating processing of the acquired sample within the housing such that the processing is in the housing in the fluid inside the conduit, (c) accepting the processed sample from the processor and separating the processed sample into respective components such that the separation is in the housing, and (d) accepting the separated components of the processed sample and analyzing the separated components to obtain information concerning one or more components of the fluid such that the analysis is in the housing whereby the probe is affixed to the conduit.

9. The method of making chromatographic measurements at the location of sampling of a fluid in a conduit, vessel or reactor as defined in claim 8 wherein the step of acquiring a sample comprises accepting the sample via a tip engaged in the fluid, the tip having an aperture for accepting and a channel for transferring the fluid.

10. The method of making chromatographic measurements at the location of sampling of a fluid in a conduit, vessel or reactor as defined in claim 9 wherein the step of accepting the sample via a tip comprises accepting the sample via a shaped tip.

11. The method of making chromatographic measurements at the location of sampling of a fluid in a conduit, vessel or reactor as defined in claim 9 wherein the step of accepting the sample via a tip comprises accepting the sample via a tip having a shield.

12. The method of making chromatographic measurements at the location of sampling of a fluid in a conduit, vessel or reactor as defined in claim 9 wherein the step of accepting the sample via a tip comprises accepting the sample through an aperture on the side of the tip.

13. The method of making chromatographic measurements at the location of sampling of a fluid in a conduit, vessel or reactor as defined in claim 12 wherein the step of accepting the sample via a tip comprises accepting the sample through an aperture on the side of the tip having a geometric shape.

14. The method of making chromatographic measurements at the location of sampling of a fluid in a conduit, vessel or reactor as defined in claim 13 wherein the step of accepting the sample via a tip comprises accepting the sample through an aperture on the end of the tip.

15. The method of making chromatographic measurements at the location of sampling of a fluid in a conduit, vessel or reactor as defined in claim 13 wherein the step of accepting the sample via a tip comprises accepting the sample through an aperture on the end of the tip having a geometric shape.

16. The method of making chromatographic measurements at the location of sampling of a fluid in a conduit, vessel or reactor as defined in claim 8 wherein the step of acquiring a sample comprises accepting the sample via a plunger removeably engaged in the fluid.

17. The method of making chromatographic measurements at the location of sampling of a fluid in a conduit, vessel or reactor as defined in claim 16 wherein the step of accepting the sample via a plunger comprises accepting the sample via a shaped plunger.

18. The method of making chromatographic measurements at the location of sampling of a fluid in a conduit, vessel or reactor as defined in claim 16 wherein the step of accepting the sample via a plunger comprises accepting the sample via a plunger having a shield.

19. The method of making chromatographic measurements at the location of sampling of a fluid in a conduit, vessel or reactor as defined in claim 16 wherein the step of accepting the sample via a plunger removeably engaged in the fluid comprises accepting the sample via a groove on the plunger.

20. The method of making chromatographic measurements at the location of sampling of a fluid in a conduit, vessel or reactor as defined in claim 16 wherein the step of accepting the sample via a plunger removeably engaged in the fluid comprises accepting the sample via a slot on the plunger.

21. The method of making chromatographic measurements at the location of sampling of a fluid in a conduit, vessel or reactor as defined in claim 16 wherein the step of accepting the sample via a plunger removeably engaged in the fluid comprises accepting the sample via a hole in the plunger.

22. The method of making chromatographic measurements at the location of sampling of a fluid in a conduit, vessel or reactor as defined in claim 8 wherein the step of acquiring a sample comprises the step of acquiring a continuous sample.

23. The method of making chromatographic measurements at the location of sampling of a fluid in a conduit, vessel or reactor as defined in claim 8 wherein the step of accepting the sample via a tip engaged in the fluid comprises the step of accepting the sample via a porous member.

24. The method of making chromatographic measurements at the location of sampling of a fluid in a conduit, vessel or reactor as defined in claim 23 wherein the step of accepting the sample via a porous member comprises using a sintered porous member.

25. The method of making chromatographic measurements at the location of sampling of a fluid in a conduit, vessel or reactor as defined in claim 23 wherein the step of accepting the sample via a porous member comprises using a membrane.

26. The method of making chromatographic measurements at the location of sampling of a fluid in a conduit, vessel or reactor as defined in claim 23 wherein the step of accepting the sample via a porous member comprises using a woven member.

27. The method of making chromatographic measurements at the location of sampling of a fluid in a conduit, vessel or reactor as defined in claim 8 wherein the step of acquiring a sample comprises the step of acquiring a batch sample.

28. The method of making chromatographic measurements at the location of sampling of a fluid in a conduit, vessel or reactor as defined in claim 27 wherein the step of acquiring a batch sample comprises the step of securing the sample in an annular channel in operative association with a plunger.

29. The method of making chromatographic measurements at the location of sampling of a fluid in a conduit, vessel or reactor as defined in claim 27 wherein the step of acquiring a batch sample comprises the step of securing the sample in a slot in operative association with the plunger.

30. The method of making chromatographic measurements at the location of sampling of a fluid in a conduit, vessel or reactor as defined in claim 27 wherein the step of acquiring a batch sample comprises the step of securing the sample in a hole in operative association with the plunger.

31. The method of making chromatographic measurements at the location of sampling of a fluid in a conduit, vessel or reactor as defined in claim 8 wherein the step of separating the processed sample into respective components comprises the step of using a chromatographic column.

32. The method of making chromatographic measurements at the location of sampling of a fluid in a conduit, vessel or reactor as defined in claim 8 wherein the step of analyzing the separated components comprises separating the sample based upon its physical properties.

33. The method of making chromatographic measurements at the location of sampling of a fluid in a conduit, vessel or reactor as defined in claim 8 wherein the step of analyzing the separated components comprises separating the sample based upon its chemical properties.

34. The method of making chromatographic measurements at the location of sampling of a fluid in a conduit, vessel or reactor as defined in claim 8 wherein the step of analyzing the separated components comprises detecting the characteristics using the thermal conductivity of the fluid.

35. The method of making chromatographic measurements at the location of sampling of a fluid in a conduit, vessel or reactor as defined in claim 8 wherein the step of analyzing the separated components comprises detecting the characteristics by burning.

36. The method of making chromatographic measurements at the location of sampling of a fluid in a conduit, vessel or reactor as defined in claim 8 further comprising the step of preventing flame propagation between the probe and the vessel.

* * * * *